(12) United States Patent
Blaesi et al.

(10) Patent No.: US 11,478,427 B2
(45) Date of Patent: *Oct. 25, 2022

(54) DOSAGE FORM COMPRISING STRUCTURAL FRAMEWORK OF TWO-DIMENSIONAL ELEMENTS

(71) Applicant: Aron H. Blaesi, Cambridge, MA (US)

(72) Inventors: Aron H. Blaesi, Cambridge, MA (US);
Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/916,208

(22) Filed: Jun. 30, 2020

(65) Prior Publication Data
US 2020/0330388 A1    Oct. 22, 2020

Related U.S. Application Data

(63) Continuation-in-part of application No. 16/860,911, filed on Apr. 28, 2020, and a continuation-in-part of application No. PCT/US2019/052030, filed on Sep. 19, 2019, and a continuation of application No. PCT/US2019/019004, filed on Feb. 21, 2019, and a continuation-in-part of application No. 15/964,063, filed on Apr. 26, 2018, now abandoned, and a continuation-in-part of application No. 15/482,776, filed on Apr. 9, 2017, now Pat. No. 11,129,798, and a continuation-in-part of application No. PCT/US2016/058935, filed on Oct. 26, 2016.

(Continued)

(51) Int. Cl.
| | |
|---|---|
| *A61K 9/20* | (2006.01) |
| *A61K 9/24* | (2006.01) |
| *A61K 47/02* | (2006.01) |
| *A61K 47/42* | (2017.01) |
| *A61K 47/34* | (2017.01) |
| *A61K 47/38* | (2006.01) |
| *A61K 47/32* | (2006.01) |

(52) U.S. Cl.
CPC ............ *A61K 9/209* (2013.01); *A61K 9/2077* (2013.01); *A61K 47/02* (2013.01); *A61K 47/32* (2013.01); *A61K 47/34* (2013.01); *A61K 47/38* (2013.01); *A61K 47/42* (2013.01)

(58) Field of Classification Search
CPC .................................................... A61K 9/209
See application file for complete search history.

(56) References Cited

U.S. PATENT DOCUMENTS 4,291,015 A * 9/1981 Keith .................... A61K 31/415
424/435
5,471,992 A * 12/1995 Banik ................ A61B 10/0266
600/564

(Continued)

*Primary Examiner* — Benjamin J Packard

(57) ABSTRACT

The most prevalent pharmaceutical dosage forms at present, the oral-delivery tablets, are granular solids. An inherent limitation of such granular solids for drug release applications is the unpredictability of the microstructure. As a result, the drug release rate and other properties are difficult to control, and their range is also limited. Presented herein, therefore, is a solid dosage form with predictable microstructure and properties. The dosage form includes a drug-containing solid comprising a three dimensional structural framework of one or more two-dimensional structural elements or sheets.

22 Claims, 16 Drawing Sheets

Related U.S. Application Data

(60) Provisional application No. 62/893,178, filed on Aug. 28, 2019, provisional application No. 62/856,073, filed on Jun. 2, 2019, provisional application No. 62/733,624, filed on Sep. 19, 2018, provisional application No. 62/633,602, filed on Feb. 21, 2018, provisional application No. 62/468,888, filed on Mar. 8, 2017, provisional application No. 62/446,431, filed on Jan. 14, 2017, provisional application No. 62/377,068, filed on Aug. 19, 2016, provisional application No. 62/246,470, filed on Oct. 26, 2015.

(56) References Cited

U.S. PATENT DOCUMENTS

| | | | |
|---|---|---|---|
| 6,416,740 B1 * | 7/2002 | Unger | A61K 49/223 |
| | | | 424/9.5 |
| 2003/0021845 A1 * | 1/2003 | Friedman | A61P 3/02 |
| | | | 424/470 |
| 2003/0035833 A1 * | 2/2003 | He | A61K 9/0007 |
| | | | 424/466 |
| 2004/0028732 A1 * | 2/2004 | Falkenhausen | A61P 25/30 |
| | | | 424/468 |

\* cited by examiner

DOSAGE FORM COMPRISING STRUCTURAL FRAMEWORK OF TWO-DIMENSIONAL ELEMENTS

CROSS-REFERENCE TO RELATED APPLICATIONS

This application is a continuation-in-part of, and incorporates herein by reference in its entirety, the U.S. application Ser. No. 15/964,063 filed on Apr. 26, 2018 and titled "Dosage form comprising two-dimensional structural elements", which is a continuation-in-part of the International Application No. PCT/US16/58935 filed on Oct. 26, 2016 and titled "Solid Dosage Form for Immediate Drug Release and Apparatus and Method for Manufacture thereof" which claims priority to and the benefit of the U.S. provisional application Nos. 62/246,470 filed Oct. 26, 2015, and U.S. 62/377,068 filed on Aug. 19, 2016. All foregoing applications are hereby incorporated by reference in their entirety.

This application is also a continuation-in-part of, and incorporates herein by reference in its entirety, the U.S. application Ser. No. 15/482,776 filed on Apr. 9, 2017 and titled "Fibrous dosage form", which claims priority to and the benefit of the U.S. provisional application Nos. U.S. 62/446,431 filed on Jan. 14, 2017, and U.S. 62/468,888 filed on Mar. 8, 2017. All foregoing applications are hereby incorporated by reference in their entirety.

This application is also a continuation-in-part of, and incorporates herein by reference in its entirety, the U.S. application Ser. No. 16/860,911 filed on Apr. 28, 2020, and titled "Expandable structured dosage form for immediate drug delivery", which is a continuation of the International Application No. PCT/US19/19004 filed on Feb. 21, 2019, and titled "Expanding structured dosage form", which claims priority to and the benefit of the U.S. Provisional Application No. 62/633,602 filed on Feb. 21, 2018, and the U.S. Provisional Application No. 62/733,624 filed on Sep. 19, 2018. All foregoing applications are hereby incorporated by reference in their entirety.

This application is also a continuation-in-part of, and incorporates herein by reference in its entirety, the International Application No. PCT/US19/52030 filed on Sep. 19, 2019, and titled "Dosage form comprising structured solid-solution framework of sparingly-soluble drug and method for manufacture thereof", which claims priority to and the benefit of the U.S. Provisional Application No. 62/856,073 filed on Jun. 2, 2019, and the U.S. Provisional Application No. 62/893,178 filed on Aug. 28, 2019. All foregoing applications are hereby incorporated by reference in their entirety.

This application is related to, and incorporates herein by reference in its entirety, the International Application No. PCT/US17/47703 filed on Aug. 19, 2017 and titled "Method and apparatus for the manufacture of fibrous dosage forms". Further, this application is related to, and incorporates herein by reference in its entirety, the International Application No. PCT/US17/41609 filed on Jul. 11, 2017 and titled "Method and apparatus for the manufacture of cellular solids".

FIELD OF THE INVENTION

This invention relates generally to microstructures and compositions for drug release. In certain embodiments, the invention relates to solid dosage forms comprising at least one two-dimensional structural element.

BACKGROUND OF THE INVENTION

The most prevalent pharmaceutical dosage forms at present, the oral immediate-release tablets, are porous solids consisting of compacted drug and excipient powders. Although powder processing is extensively used in the manufacture of oral dosage forms, an inherent limitation of compacted powders is the non-deterministic porosity. As a result, the dosage form microstructure and properties (e.g., the drug content, drug release rate, etc.) are difficult to control tightly, and their range is also limited.

To overcome such limitations, therefore, in the U.S. patent application Ser. No. 15/482,776, and the publications in Mater. Sci. Eng. C 84 (2018) 218-229 and Eur. J. Pharm. Biopharm. 130 (2018) 345-358, the present inventors (Blaesi and Saka) have introduced fibrous dosage forms. These dosage forms comprise solid frameworks of a drug-excipient composite (or a solid solution) and gas-filled void space. It was shown that both the microstructure and the drug release rate are predictable and precisely controllable. The release rate was predominantly determined by the fiber radius, the physico-chemical properties of the excipient, the connectivity of the void space, and the inter-fiber spacing.

A related structural framework that enables predictable properties, a greater range of properties, and faster and more economical development and manufacture of dosage forms at reproducible quality, among others, comprises two-dimensional structural elements or sheets. Therefore, in this disclosure, microstructures and compositions of dosage forms comprising two-dimensional structural elements are presented. It may be noted that the terms "two-dimensional structural elements", "two-dimensional elements", "elements", and "sheets" are used interchangeably herein.

SUMMARY OF THE INVENTION

In a first aspect, the present invention provides a pharmaceutical dosage form comprising a drug-containing solid having an outer surface and an internal structure contiguous with and terminating at said outer surface; said internal structure comprising a continuous, three dimensional structural skeleton of one or more stacked sheets, wherein average thickness of said sheets is no greater than 1 mm; said sheets comprising at least one active ingredient and at least one excipient through their thickness, wherein at least one excipient has a solubility in physiological fluid under physiological conditions no less than 1 g/l; said sheets further comprising segments separated and spaced from adjoining segments by free spacings, said free spacings defining one or more interconnected free spaces across or through the drug-containing solid; and said one or more interconnected free spaces terminating at said outer surface and filled with at least a gas.

In certain embodiments, the internal structure further comprises one or more zero-dimensional elements.

In certain embodiments, the internal structure further comprises one or more zero-dimensional elements bonded to and positioned between sheets or segments thereof to separate the sheets or segments thereof by free spacings.

In certain embodiments, the internal structure further comprises one or more one-dimensional elements or fibers.

In certain embodiments, the internal structure further comprises one or more fibers bonded to and positioned between the sheets or segments thereof to separate the sheets or segments thereof by free spacings.

In certain embodiments, at least one element or segment thereof is bonded to another element or segment by inter-diffusion of molecules between said elements or segments.

In certain embodiments, the free spacing between the segments is so that the percolation time of physiological/ body fluid into one or more interconnected free spaces of the dosage form is no greater than 900 seconds under physiological conditions.

In certain embodiments, the average effective free spacing between segments across an interconnected free space is in the range between 1 µm and 4 mm.

In certain embodiments, the average effective free spacing between the segments across an interconnected free space on average is greater than 0.1 µm.

In certain embodiments, the effective free spacing (e.g. the pore size or pore diameter) across an interconnected free space or open pore network is greater than 5 µm (e.g., greater than 10 µm, or greater than 20 µm, or greater than 30 µm).

In some embodiments, the effective free spacing (e.g. the pore size or pore diameter) across an interconnected free space or open pore network is in the range 5 µm-2.5 mm (e.g., 5-2 mm, 5 µm-1.5 mm, or 5 µm-1.25 mm, or 5 µm-1 mm, or 10 µm-1.5 mm, or 20 µm-1.5 mm).

In some embodiments, the effective free spacing between segments across an interconnected free space or open pore network on average is in the range 1 µm-3 mm.

In some embodiments, the free spacing between segments of the structural elements (e.g., sheets, fibers, beads, etc.) is precisely controlled across or through the drug-containing solid.

In some embodiments, the three dimensional structural skeleton or framework extends over a length, width, and thickness at least two (e.g., at least three, or at least four, or at least five, or at least six, or at least seven) times the average thickness of the one or more sheets.

In certain embodiments, the three dimensional structural skeleton or framework of sheets comprises an ordered structure.

In certain embodiments, the thickness of at least one sheet is precisely controlled.

In certain embodiments, the position of at least one sheet or at least one segment in the internal structure is precisely controlled.

In certain embodiments, at least one element or segment thereof is in contact with another element or segment, and wherein the number of contacts between elements or segments thereof within the drug-containing solid is precisely controlled.

In certain embodiments, at least one excipient is wettable by a physiological/body fluid under physiological conditions.

In certain embodiments, at least one excipient is soluble in a physiological/body fluid and comprises a solubility greater than 5 g/l in said physiological/body fluid under physiological conditions.

In certain embodiments, dissolved molecules of the soluble excipient comprise a diffusivity greater than $0.2 \times 10^{-12}$ m$^2$/s in a physiological/body fluid under physiological conditions.

In certain embodiments, at least one excipient is absorptive of a physiological/body fluid, and wherein rate of penetration of the physiological/body fluid into a sheet or said absorptive excipient under physiological conditions is greater than the average thickness of said sheet divided by 3600 seconds.

In certain embodiments, at least one excipient is absorptive of a physiological/body fluid, and wherein an effective diffusivity of physiological/body fluid in a sheet or said absorptive excipient is greater than $0.5 \times 10^{-11}$ m$^2$/s under physiological conditions.

In certain embodiments, at least one excipient transitions from solid to a fluidic or gel consistency solution upon contact with a volume of physiological/body fluid equal to the volume of the one or more interconnected free spaces of the drug-containing solid, said solution having a viscosity less than 500 Pa·s under physiological conditions.

In certain embodiments, at least one excipient is selected from the group comprising polyethylene glycol (PEG), polyethylene oxide, polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, or butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, or hydroxypropyl methylcellulose), starch, polylactide-co-glycolide, polyvinyl caprolactam-polyvinyl acetate-polyethylene glycol graft copolymer, lactose, starch derivatives (e.g., pregelatinized starch or sodium starch glycolate), chitosan, pectin, polyols (e.g., lactitol, maltitol, mannitol, isomalt), acrylic acid crosslinked with allyl sucrose or allyl pentaerythritol (e.g., carbopol), and polyacrylic acid.

In certain embodiments, an interconnected free space is filled with a matter selected from the group comprising gas, liquid, or solid, or combinations thereof, and wherein said matter is partially or entirely removed upon contact with a physiological/body fluid under physiological conditions.

In certain embodiments, the gas comprises at least one of air, nitrogen, $CO_2$, argon, or oxygen.

In certain embodiments, at least one interconnected free space or open pore network extends over a length greater than half the thickness of the drug-containing solid.

In certain embodiments, an interconnected free space forms an open pore network that extends over a length at least equal to the thickness of the drug-containing solid.

In certain embodiments, an interconnected free space forms an open pore network that extends over a length and width at least half the thickness of the drug-containing solid.

In certain embodiments, an interconnected free space forms a three-dimensional open pore network that extends over a length, width, and thickness at least half the thickness of the drug-containing solid.

In certain embodiments, at least one interconnected free space or open pore network extends across or through the drug-containing solid.

In certain embodiments, an interconnected free space forms an open pore network that extends over the entire length, width, and thickness of the drug-containing solid.

In certain embodiments, an open pore network comprises or occupies at least 40 percent (e.g., at least 50 percent, or at least 60 percent or at least 70 percent or at least 80 percent) of the free space of the drug-containing solid (e.g., at least 40 percent (e.g., at least 50 percent, or at least 60 percent or at least 70 percent or at least 80 percent or 100 percent) of the free space of the drug-containing solid are part of the same open pore network).

In certain embodiments, the free space is contiguous.

In certain embodiments, the dosage form or drug-containing solid comprises a coating covering its outer surface.

In a second aspect, the present invention provides a pharmaceutical dosage form comprising a drug-containing solid having an outer surface and an internal structure contiguous with and terminating at said outer surface; said internal structure comprising a continuous, three dimensional structural framework of one or more sheets, wherein average thickness of said sheets is no greater than 1 mm;

said sheets comprising at least one active ingredient and at least one excipient through their thickness, wherein at least one excipient has a solubility in physiological fluid under physiological conditions no less than 30 g/l; said sheets further comprising segments separated and spaced from adjoining segments by free spacings, said free spacings defining one or more interconnected free spaces between said sheets and/or across or through the drug-containing solid; said one or more interconnected free spaces filled with at least a gas; and at least one of said one or more interconnected free spaces terminating at said outer surface, and extending over a length and width at least half the thickness of the drug-containing solid.

In a third aspect, the present invention provides a pharmaceutical dosage form comprising an outer surface and an internal structure contiguous with and terminating at said outer surface; said internal structure comprising a continuous, three dimensional structural framework of one or more sheets and one or more fibers or one or more beads; said sheets comprising at least one active ingredient and at least one excipient through their thickness, wherein at least one excipient has a solubility in physiological fluid under physiological conditions no less than 1 g/l; said fibers or beads bonded to and positioned between one or more sheets so that the sheets are separated and spaced from adjoining sheets by free spacings, said free spacings defining one or more interconnected free spaces across or through the drug-containing solid; and said one or more interconnected free spaces filled with at least a gas and terminating at said outer surface.

Elements of embodiments described with respect to one aspect of the invention can be applied with respect to another aspect. By way of example but not by way of limitation, certain embodiments of the claims described with respect to the first aspect can include features of the claims described with respect to the second or third aspect, and vice versa.

This invention may be better understood by reference to the accompanying drawings, attention being called to the fact that the drawings are primarily for illustration, and should not be regarded as limiting.

BRIEF DESCRIPTION OF THE DRAWINGS

The objects, embodiments, features, and advantages of the present invention are more fully understood when considered in conjunction with the following accompanying drawings.

DEFINITIONS

Figure 1:
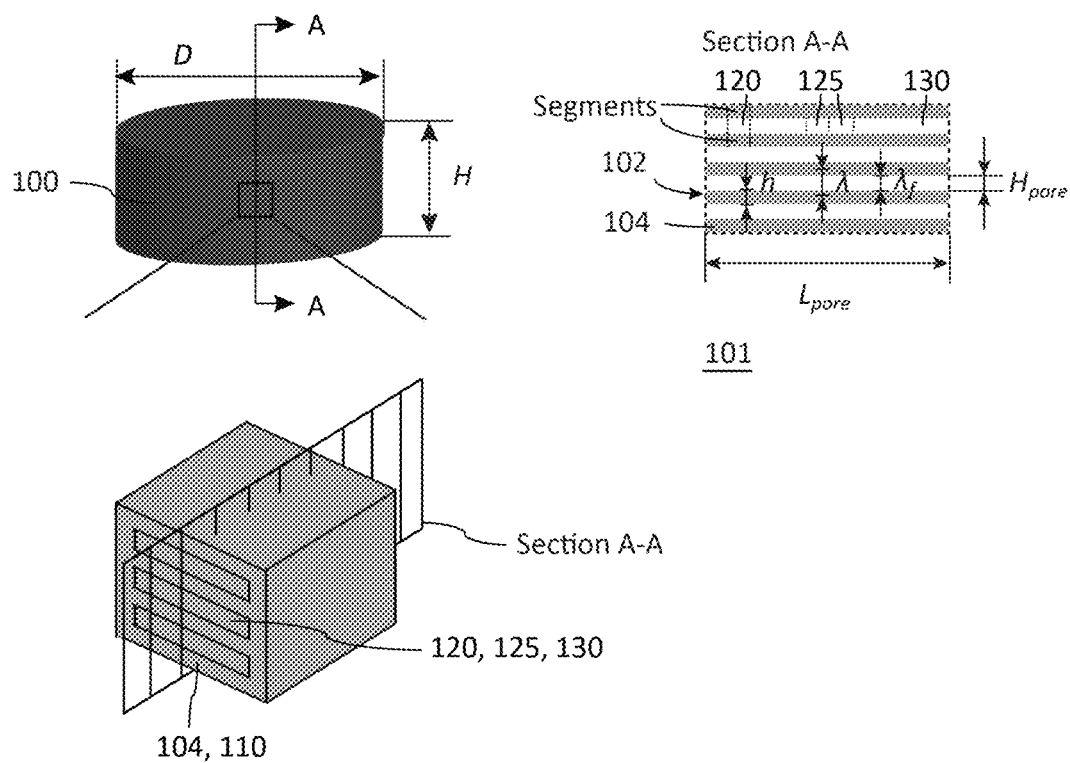
FIG. 1 shows a non-limiting schematic of a dosage form and its microstructure comprising a three dimensional structural skeleton or framework of one or more stacked sheets according to this invention.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients" and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

Furthermore, in the context of the invention herein, a three dimensional structural skeleton or framework of one or more two-dimensional structural elements (also referred to herein as "three dimensional structural skeleton of one or more sheets") generally comprises a structure (e.g., an assembly or an assemblage or an arrangement) of one or more two-dimensional structural elements that extends over a length, width, and thickness greater than 100 µm. This includes, but is not limited to structures of one or more two-dimensional structural elements that extend over a length, width, and thickness greater than 200 µm, or greater than 500 µm, or greater than 700 µm, or greater than 1 mm, or greater than 1.25 mm, or greater than 1.5 mm, or greater than 2 mm.

In some embodiments, moreover, a three dimensional structural skeleton or framework (or network) of drug-containing elements may comprise a drug-containing structure (e.g., an assembly or an assemblage of one or more elements) that extends over a length, width, and thickness greater than the average thickness of at least one element (or at least one segment) in the three dimensional structural framework (or network) of elements. This includes, but is not limited to drug-containing structures that extend over a length, width, and thickness greater than 1.5, or greater than 2, or greater than 2.5, or greater than 3, or greater than 3.5, or greater than 4, or greater than 5 times the average thickness of at least one element (or at least one segment) in the three dimensional structural framework (or network) of elements.

As used herein, the terms "two-dimensional structural element", "two-dimensional element", "two-dimensional elements", "2D-elements", "one or more two-dimensional elements", "one or more drug-containing two-dimensional elements", "drug-containing two-dimensional elements", "element" or "elements", and "sheet" or "sheets" are used interchangeably. They are understood as the solid, drug-containing structural elements (or building blocks) that make up the three dimensional structural framework (e.g., the dosage form structure). A two-dimensional structural element is referred to as having a length and width much greater than its thickness. In the present disclosure, the length and width of a two-dimensional structural element are greater than 2 times its thickness. This includes, but is not limited to a length and with greater than 3 times its thickness, or greater than 4 times its thickness, or greater than 5 times its thickness. An example of a two-dimensional element is a "sheet".

Moreover, as used herein, the term "segment" generally refers to a fraction of a two-dimensional element along the length or width of said element.

As used herein, a one-dimensional structural element is referred to as having a length much greater than its width or thickness. In the present disclosure, the length of a one-dimensional structural element is greater than 2 times its width and thickness. An example of such an element is a "fiber". It may be noted that the terms "1-dimensional element", "one-dimensional structural element", "one-dimensional element", "1D-element", and "element" are used interchangeably herein. A zero-dimensional structural element is referred to as having a length and width of the order of its thickness. In the present disclosure, the length and width of a zero-dimensional structural element are no greater than 2 times its thickness. Furthermore, the thickness of a zero-dimensional element is less than 2.5 mm. Examples of such zero-dimensional elements are "particles" or "beads" and include polyhedra, spheroids, ellipsoids, or clusters thereof. It may be noted that the terms "0-dimensional element", "zero-dimensional structural element", "zero-dimensional element", "0D-element", and "element" are used interchangeably herein.

In some embodiments herein, the term "element" may refer to a two dimensional element, or a one-dimensional element, or a zero-dimensional element.

In the invention herein, the terms "interconnected free spaces" and "open pore network" in the drug-containing solid are used interchangeably, and are also referred to as "interconnected pore network", "network of open channels", or "open channels of free space" in the drug-containing solid. An "interconnected free space" or "open pore network" combines or unites a plurality of adjacent free spaces between or across sheets, so that each point in the open pore network is accessible from another point in the open pore network, and a continuous, open path exists from any point in the open pore network to any other point in the open pore network.

Finally, as used herein, the terms "dissolution medium", "physiological/body fluid", "dissolution fluid", "medium", "fluid", and "penetrant" are used interchangeably. They are understood as any fluid produced by or contained in a human body under physiological conditions, or any fluid that resembles a fluid produced by or contained in a human body under physiological conditions. Examples include, but are not limited to: water, saliva, stomach fluid, gastrointestinal fluid, saline, etc. at a temperature of 37° C. and a pH value adjusted to the specific physiological condition.

DETAILED DESCRIPTION OF THE INVENTION

Dosage Form Structures

FIG. 1 presents a non-limiting example of a pharmaceutical dosage form 100 comprising a drug-containing solid 101 having an outer surface 102 and an internal structure 104 contiguous with and terminating at said outer surface 104. The internal structure comprises a continuous, three dimensional structural skeleton or framework of one or more stacked sheets 110. Said sheets 110 include at least one active ingredient and at least one excipient through their thickness. Said sheets 110 further comprise segments separated and spaced from adjoining segments by free spacings, $\lambda_f$, said free spacings define one or more interconnected free spaces 120 between said sheets 110 and/or through or across the drug-containing solid 101. The one or more interconnected free spaces 120 are filled with at least a gas, and terminate at said outer surface 102.

The arrangement (or structure, or three dimensional structural framework, or three dimensional structural skeleton) shown is ordered and provides control of two structural variables essential for tailoring the properties of the drug-containing solid 101 or dosage form 100: the thickness of the sheets 110, h, (or the average thickness, $h_0$) and the spacing between the sheets or segments thereof, $\lambda$ (or alternatively the free spacing, $\lambda_f$).

Moreover, because a plurality of adjacent free spaces 125 combine to define one or more interconnected free spaces, at least one open pore network 130 is formed. Said at least one open pore network or interconnected free space 120, 125, 130 may extend over the entire length (e.g., over an entire length, or over an entire width, or over an entire thickness) of the drug-containing solid 101 or dosage form 100. Thus the length, $L_{pore}$, over which said at least one open pore network 130 extends may be the same as the length or diameter, D, of the dosage form 100 or drug-containing solid 101. No walls (e.g., walls comprising the three dimensional structural framework 104 of sheets) must be ruptured to obtain an interconnected cluster of free space 120, 125, 130 (e.g., an open channel of free space) from the outer surface 102 of the drug-containing solid 101 to a point or position (or to any point) in the free space 120, 125, 130. The interconnected free space 120, 125, 130 between the segments is intrinsically connected to the outer surface 102 of the drug-containing solid 101 or dosage form 100.

In the non-limiting example shown in FIG. 1, however, the thickness, $H_{pore}$, over which said at least one open pore network or interconnected free space 120, 125, 130 may extend is much smaller than the thickness, H, of the dosage form 100 or drug-containing solid 101. Thus it may be necessary to rupture one or more walls (e.g., walls comprising the three dimensional structural framework 104 of sheets) to obtain an interconnected cluster of free space (e.g., an open channel of free space) from a point or position within a free space to another point or position in a free space.

Figure 2:
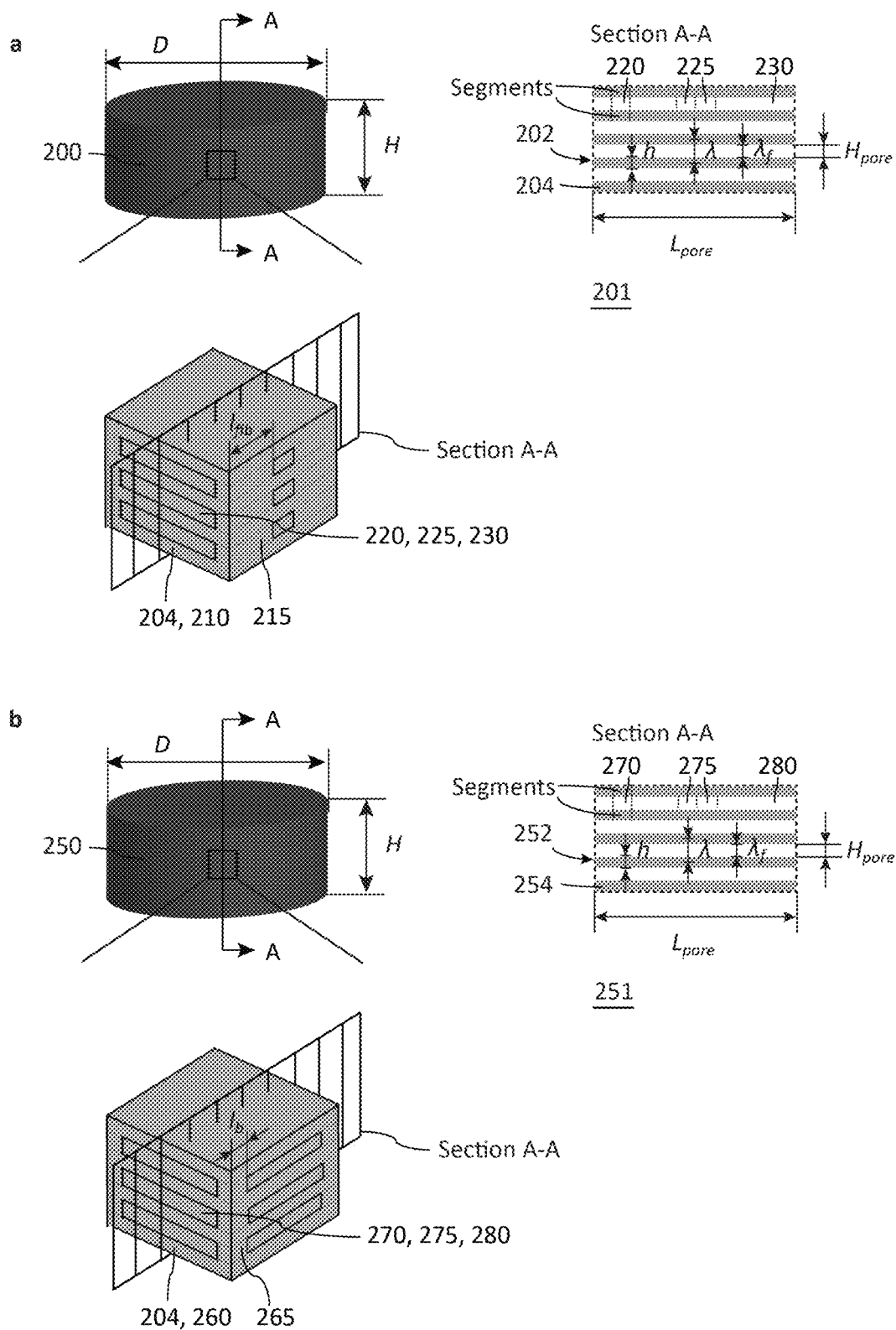
FIG. 2 presents further non-limiting schematics of dosage forms and microstructures according to the invention herein.
Figure 3:
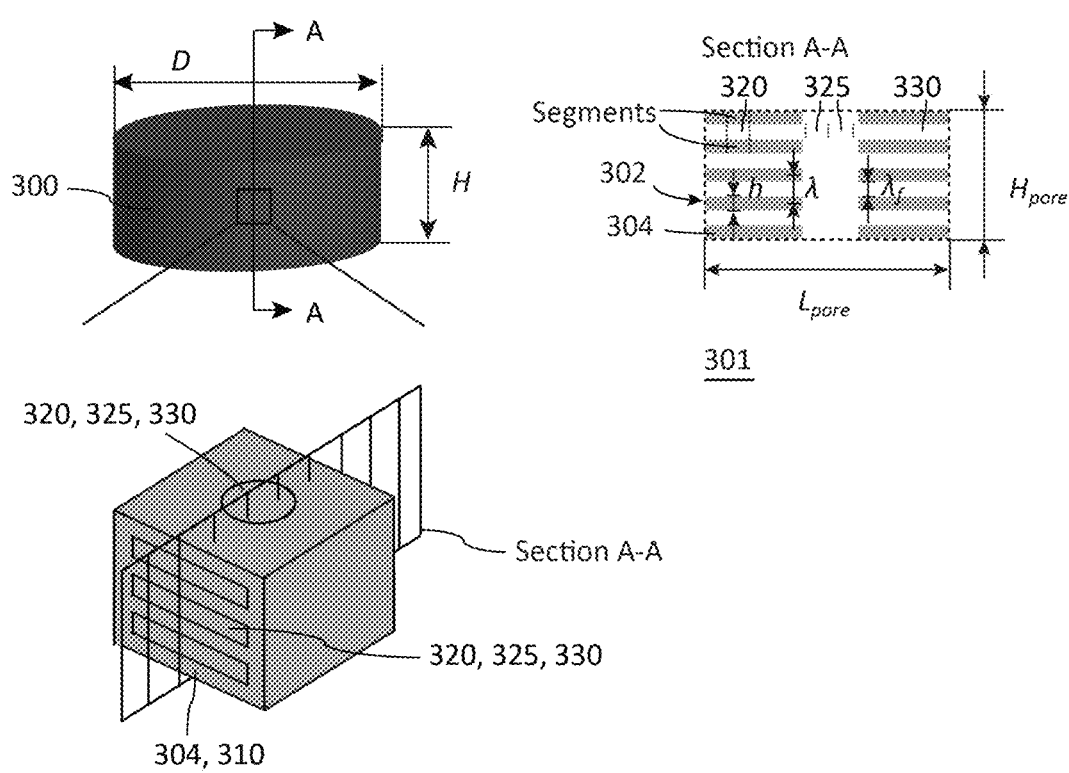
FIG. 3 is another non-limiting schematic of a dosage form and its microstructure comprising a three dimensional structural skeleton or framework of one or more stacked sheets according to this invention.

Non-limiting examples of structures where interconnected free spaces extend over an entire length and width (e.g., an entire length and thickness, or an entire width and thickness, etc.) of the drug-containing solid are shown in FIGS. 2 and 3. FIGS. 2*a* and 2*b* present a non-limiting example of a pharmaceutical dosage form 200, 250 comprising a drug-containing solid 201, 251 having an outer surface 202, 252 and an internal structure 204, 254 contiguous with and terminating at said outer surface 202, 252. The internal structure 204, 254 comprises a continuous, three dimensional structural skeleton or framework of one or more sheets 210 and one or more fibers 215 or one or more beads 265. Said sheets 210 include at least one active ingredient and at least one excipient through their thickness. Said fibers 215 or beads 265 are bonded to and positioned between one or more sheets 210 so that the sheets (or segments of a sheet) are separated and spaced from adjoining sheets (or adjoining segments of a sheet) by free spacings, $\lambda_f$, said free spacings define at least an interconnected free space 220, 270 between the sheets (or between adjoining segments of a sheet), and/or through or across the drug-containing solid 201, 251. The at least one interconnected free space 220, 270 is filled with at least a gas and terminates at said outer surface 202, 252. Moreover, because the length of the fibers, $l_{fib}$, or the length of the beads, $l_b$, is smaller than a length (or a width or a thickness) of the drug-containing solid or dosage form, adjacent free spaces 225, 275 combine to form an interconnected free space or open pore network 220, 225, 230, 270, 275, 280 that may extend over at least a length and a width (e.g., a length and a thickness, or a width and a thickness, etc.) of the drug-containing solid 201, 251.

FIG. 3 presents another non-limiting example of a pharmaceutical dosage form 300 comprising a drug-containing solid 301 having an outer surface 302 and an internal structure 304 contiguous with and terminating at said outer surface 302. The internal structure 302 comprises a continuous, three dimensional structural skeleton or framework of one or more sheets 310. Said sheets 310 include at least one active ingredient and at least one excipient through their thickness. Said sheets 310 further comprise segments separated and spaced from adjoining segments by free spacings, $\lambda_f$, said free spacings define one or more interconnected free spaces 320 between the sheets 310. Said sheets or segments thereof further comprise at least a perforation (e.g., one or more perforations or at least a perforation in each layer of the stacked layers of sheets, etc.) so that interconnected free spaces 320 combine or unite across sheets. Thus because adjacent free spaces 325, 375 combine between and across sheets an interconnected free space or open pore network 320, 325, 330, 370, 375, 380 that may extend over at least a length and a width (e.g., a length and a thickness, or a width and a thickness, etc.) of the drug-containing solid 301, 351 may be formed. The interconnected free space 320 is further filled with a gas, and terminates at said outer surface 302.

Figure 4:
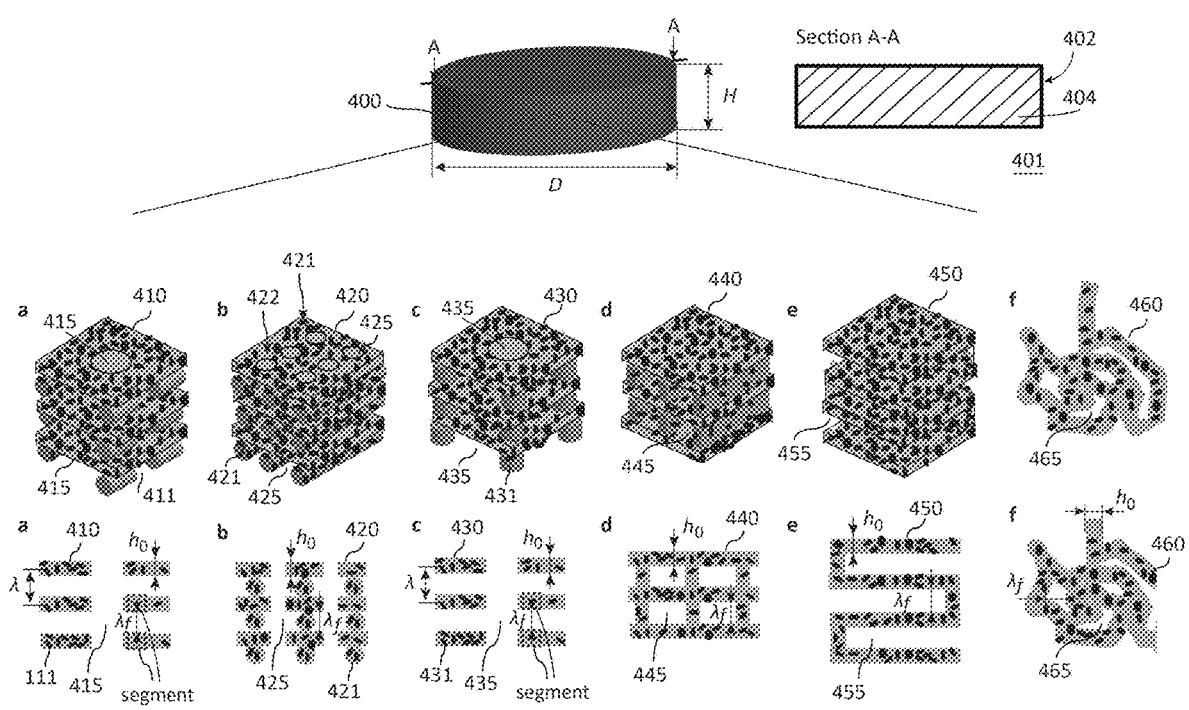
FIG. 4 shows additional non-limiting schematics of dosage forms and microstructures according to the invention herein.

FIG. 4*a* presents a non-limiting example of a pharmaceutical dosage form 400 comprising a drug-containing solid 401 having an outer surface 402 and an internal structure 404 contiguous with and terminating at said outer surface 402. The internal structure 404 comprises a continuous, three dimensional structural skeleton or framework of one or more sheets 410 and one or more fibers 413. Said sheets 410 include at least one active ingredient 411 and at least one excipient 412 through their thickness. Said fibers 413 are bonded to and positioned between one or more sheets 410 so that the sheets (or segments of a sheet) are separated and spaced from adjoining sheets (or adjoining segments of a sheet) by free spacings; said free spacings define an interconnected free space 415 between the sheets (or between adjoining segments of a sheet), and/or through or across the drug-containing solid 401. Said sheets or segments thereof further comprise at least a perforation 416 (e.g., one or more perforations or at least a perforation in each layer of the stacked layers of sheets, etc.) so that interconnected free spaces 415, 416 combine and unite across sheets 410. Moreover, because the free spaces combine between and across sheets, and the length of the fibers, $l_{fib}$, is smaller than a length (or a width or a thickness) of the drug-containing solid 401 or dosage form 400, an interconnected free space or open pore network 415, 416 that may extend over a length, width, and thickness of the dosage form 400 or drug-containing solid 401 is formed. The interconnected free space 415, 416 further is filled with at least a gas and terminates at said outer surface 402.

FIGS. 4*b*-4*f* show additional non-limiting examples of pharmaceutical dosage forms 400 comprising a drug-containing solid 401 having an outer surface 402 and an internal structure 404 contiguous with and terminating at said outer surface 402. The internal structure 404 comprises a continuous, three dimensional structural skeleton or framework of one or more sheets 420, 430, 440, 450, 460. Said sheets 420, 430, 440, 450, 460 include at least one active ingredient 421, 431, 441, 451, 461 and at least one excipient 422, 432, 442, 452, 462 through their thickness. Said sheets 420, 430, 440, 450, 460 further comprise segments separated and spaced from adjoining segments by free spacings; said free spacings define one or more interconnected free spaces 425, 435, 445, 455, 465 between said sheets 420, 430, 440, 450, 460, and across or through the drug-containing solid 401. The one or more interconnected free spaces 425, 435, 445, 455, 465 are filled with at least a gas, and terminate at said outer surface 402. The one or more interconnected free spaces 425, 435, 445, 455, 465 may further extend over at least a length of the drug-containing solid 401.

More specifically, FIG. 4*b* shows a dosage form 400 or drug-containing solid 401 or internal structure 402 with parallel arrangement (e.g. a three dimensional structural framework with parallel arrangement) of sheets 420 with rectangular cross section. In the specific example, moreover, the sheets 420 (or segments thereof) are stacked. In between the sheets (or segments thereof) 110 are layers of fibers 423 to separate the sheets 420 or segments thereof from adjoining sheets or segments thereof by free spacings, $\lambda_f$, defining interconnected free spaces 425 in the drug-containing solid 401. The sheets 420 further comprise perforations 426 in each layer of the stacked layers of sheets, so that interconnected free spaces 425, 426 combine across sheets 420. The interconnected free space or open pore network 425, 426 may thus extend over a length and width of the dosage form 400 or drug-containing solid 401. In the given example, moreover, the fibers 421 (or segments of a fiber) in a layer are parallel arranged and unidirectionally aligned.

FIG. 4*c* shows a dosage form 400 or drug-containing solid 401 having layers of one or more beads 431 in between the sheets (or segments thereof) 430 to separate the sheets 430 or segments thereof from adjoining sheets or segments thereof by free spacings, $\lambda_f$. In the framework shown the length of the beads, $l_b$, is smaller than a length (or a width or a thickness) of the drug-containing solid or dosage form. Moreover, the sheets 430 comprise perforations 436 in each layer of the stacked layers of sheets, so that interconnected free spaces 435, 436 combine across sheets 430. Thus the free spacings define an interconnected free space 435, 436 that may extend over a length, width, and thickness of the drug-containing solid 401.

FIG. 4d presents a dosage form 400 or drug-containing solid 401 having one or more layers of fibers with rectangular cross section 443 in between the sheets (or segments thereof) 440 to separate the sheets or segments thereof from adjoining sheets or segments thereof by free spacings, $\lambda_f$. Moreover, a length or width of the sheets, $l_{sheet}$, is smaller than a length (or a width or a thickness) of the drug-containing solid 401 or dosage form 400. Thus interconnected free spaces 445 combine across sheets 430. The free spacings define an interconnected free space 445 that may extend over at least a length and a width (e.g., at least a length and a thickness, or at least a width and a thickness, etc.) of the drug-containing solid 401.

FIG. 4e shows a non-limiting example of a continuous sheet 450 that makes up the three-dimensional structural framework. The structure shown in FIG. 4e and all other non-limiting structures shown in FIGS. 4a-4d may be considered ordered or regular (e.g., the sheets are orderly or regularly arranged, or the position or arrangement of the sheets is controlled, etc.). Ordered structures are preferred herein because they allow better control of the properties of the dosage form. A structure with random or almost random arrangement/assembly of one or more sheets 460 (e.g. a structure that is disordered) is shown in FIG. 4f.

Figure 5:
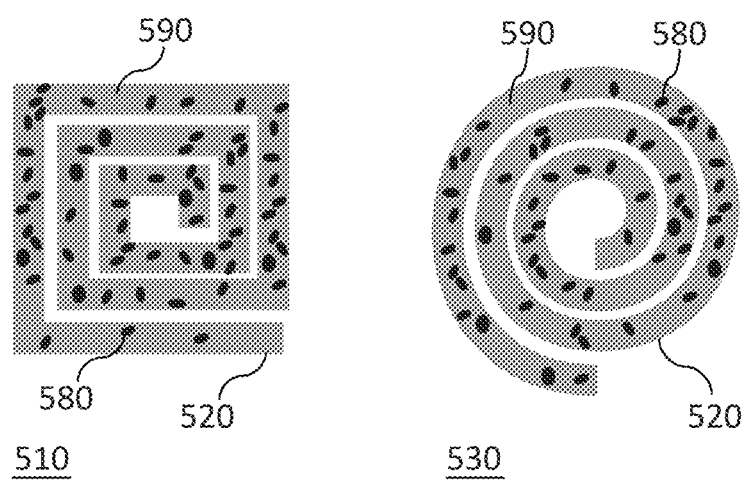
FIG. 5 presents yet further non-limiting schematics of microstructures according to this invention.

Other non-limiting examples of three dimensional structural frameworks of one or more orderly arranged drug-containing sheets as disclosed herein are shown in FIG. 5. FIG. 5 presents a top view of a structural framework of drug-containing sheets 520 forming a rectangular structure 510, as well as a top view of a structural framework of drug-containing sheets 520 forming a circular (or elliptical) structure 530. Both frameworks comprise segments separated and spaced from adjoining segments by free spacings defining an interconnected free space 525 between the sheets 520 and across or through the framework or drug-containing solid.

Therefore, in the structures disclosed herein, an interconnected free space or open pore network can extend over a length, or over a length and a width, or over a length, width, and thickness, at least half the thickness of the drug-containing solid. This includes, but is not limited to an interconnected free space or open pore network extending over a length, or over a length and width, or over a length, width, and thickness, at least equal to the thickness of the drug-containing solid. In preferred embodiments, moreover, an open pore network typically extends over an entire length, or over an entire length and an entire width, or over an entire length, width, and thickness, of the drug-containing solid, so that all free spaces are open and interconnected forming a single interconnected pore network.

It may further be noted that the directions of a length and a width, a length and a thickness, a width and a thickness, and a length, a width, and a thickness of an interconnected free space or open pore network generally are perpendicular to each other. Accordingly, the directions of length, width, and thickness of an interconnected free space or open pore network may form a rectangular coordinate system.

Moreover, if an interconnected free space extends over a length (e.g., over a length, a width, a thickness, etc.) or over a large part of a length (e.g., over a large part of a length, a width, a thickness, etc.) of the drug-containing solid, said interconnected free space is also understood herein as "extending across or through the drug-containing solid". Thus the terms "one or more interconnected free spaces extending across or through the drug-containing solid" or "free spacings defining one or more interconnected free spaces across or through the drug-containing solid" include, but are not limited to one or more interconnected free spaces extending over at least a length at least 0.5 times, or at least 0.6 times, or at least 0.7 times, or at least 0.8 times, or at least 0.9 times, or at least 1 time a relevant length (e.g., a relevant length, width, or thickness) of the drug-containing solid.

Furthermore, because one or more interconnected free spaces may terminate at an outer surface of the drug-containing solid, in some embodiments interconnected free space or interconnected free spaces is/are accessible from the outer surface of the drug-containing solid. That is, no walls (e.g., walls comprising the three dimensional structural framework of elements) must be ruptured to obtain an interconnected free space (e.g., an open channel of free space) from the outer surface of the drug-containing solid to a point (or to any point) in the interconnected free space within the internal structure.

Also, in some embodiments, no walls (e.g., walls comprising the three dimensional structural framework of elements) must be ruptured to obtain an interconnected cluster of free space (e.g., an open channel of free space) from a point in the free space to another point (or to any point) in the free space within the internal structure. In this case, the entire free space or essentially all free spaces is/are connected. It may be noted that if all free spaces (e.g., the entire free space in the drug-containing solid) is interconnected, the free space is also referred to herein as "contiguous". Dosage forms with contiguous free space comprise a preferred embodiment of this invention.

More examples of how the sheets may be structured, arranged, or assembled would be obvious to a person of ordinary skill in the art. All of them are within the spirit and scope of this invention.

Compositions and Material Structures of Sheets

The sheets 410, 420, 430, 440, 450, 460, 520 typically consist of one or more active ingredients 421, 431, 441, 451, 461 (also referred to here as "drug"), and in most cases also one or more excipients 422, 432, 442, 452, 462 (also referred to here as "excipient"). If a sheet consists of at least one active ingredient and at least one excipient, the drug and excipient may be structured in the sheet in an ordered or "partially or completely disordered" manner. Moreover, the structural features of the drug or the excipient in the sheet may comprise any shape or geometry. By way of example but not by way of limitation, this includes particles, beads, polygons, ellipsoids, cubes, tubes, rods, sheets, etc., or combinations thereof. The features may have a size at the molecular-, nano-, micro-, meso-, or macro-scale. Thus, drug may be molecularly dissolved in excipient, excipient may be molecularly dissolved in drug, drug may be dispersed as nano- or micro-particles in an excipient, and so on.

In some embodiments, moreover, a sheet comprises a single solid matrix through its thickness.

More such examples of compositions and material structures of sheets would be obvious to a person of ordinary skill in the art. All of them are within the scope of this invention.

Drug Release from Sheets

If the composition of a sheet consists of drug only, or if the drug is interconnected in the material structure of the sheet, the drug may be in direct contact with dissolution fluid upon immersion of the sheet in a medium. Thus, in some embodiments, the drug may be released from the sheet by dissolution of drug into the medium.

Figure 6:
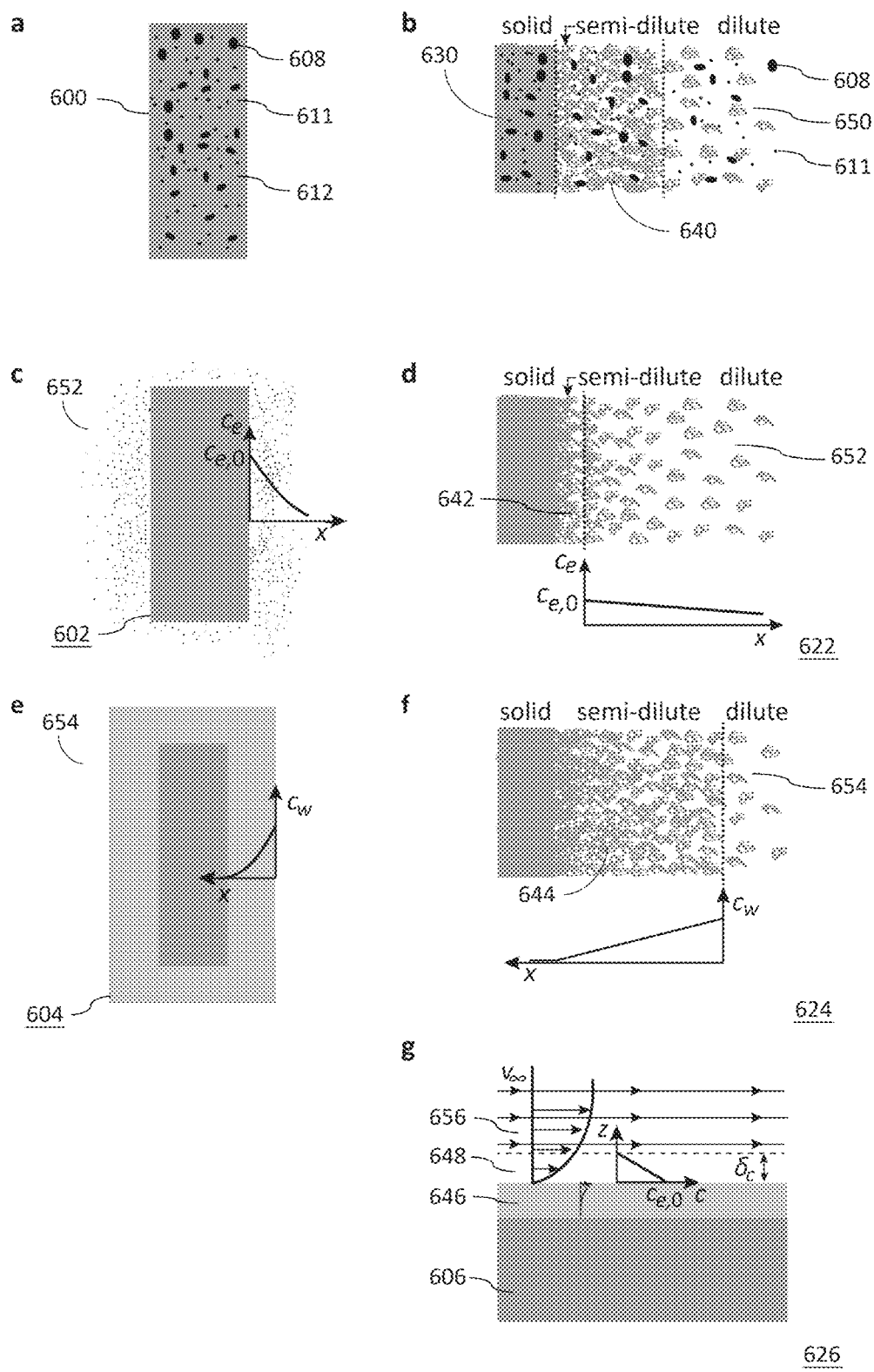
FIG. 6 schematically shows non-limiting microstructures and disintegration processes of single, two-dimensional structural element or sheets.

If the material structure of a sheet 600, however, comprises one or more discontinuous clusters of at least one drug particle 608 or at least one drug molecule 609 surrounded by a solid excipient 612 as shown in FIG. 6a, erosion or swelling of the excipient 612 is a prerequisite for drug release from the sheet 600. Two non-limiting examples of how drug may be released from such sheets 600 are presented below.

In the first non-limiting example, the excipient comprises an erodible polymer. Thus, as soon as the sheet 600 is brought in contact with dissolution medium, the medium diffuses into the excipient. The penetrant molecules (e.g., the dissolution fluid that diffused into the solid excipient) may then induce the solid excipient to swell (e.g., to increase in volume) and to transition from a solid to a fluidic or gel consistency solution. Subsequently, the polymer molecules from the gel consistency solution may diffuse or erode into the dissolution medium. The drug (e.g., a drug molecule or a drug particle) may be released from the sheet 600 as soon as the surrounding excipient has converted to dissolved molecules or a gel with polymer concentration smaller than the "interfacial concentration".

The "interfacial concentration" is referred to in this application as the polymer concentration which separates the "solid" and "liquid" regions. For a typical polymer that erodes into a dissolution fluid, the interface is diffuse, and thus the interfacial concentration is difficult to determine precisely. As schematically shown in FIG. 6b, the diffuse interface may extend over a layer 640 of non-negligible but finite thickness. It may be considered a semi-dilute gel consistency solution between the entangled, concentrated, and viscous polymer 630 (i.e., the "solid" or "semi-solid") and the dilute, low-viscosity dissolution medium 650 (i.e., the "liquid"). Thus, typically, the concentration of an eroding polymer in the semi-dilute interfacial layer 640 (e.g., the "interfacial concentration") is of the order of the disentanglement concentration, $c_p^*$, of said polymer in a dissolution medium. In some embodiments, however, if the rate at which polymer molecules at the interface are disentangled is small, the interfacial concentration may be substantially smaller than $c_p^*$. (For further information related to polymer disentanglement, see e.g., P. G. De Gennes, "Scaling concepts in polymer physics", fifth ed., Cornell University Press, 1996; or M. Doi, S. F. Edwards, "The theory of polymer dynamics", Oxford University Press, 1986).

In the second non-limiting example, the excipient comprises an absorptive or swellable polymer. Thus, upon immersion of the two-dimensional element in a dissolution fluid, the fluid diffuses into the solid polymeric excipient. The penetrant molecules (e.g., the dissolution fluid that diffused into the solid excipient) may then convert part or all of the solid drug enclosed in the polymeric excipient to dissolved drug molecules. The mobility of drug molecules may be greater in the penetrated polymeric excipient than in the excipient without penetrant. Thus the drug molecules embedded in the penetrated excipient may diffuse to the dissolution medium swiftly, and drug may be released within the specific time requirements.

More examples of drug release from two-dimensional elements would be obvious to a person of ordinary skill in the art. All of them are within the scope of this invention.

Modeling Disintegration and Drug Release

The following examples present ways by which the drug release and disintegration behavior of two-dimensional elements and dosage forms comprising two-dimensional elements may be modeled. The models will enable one of skill in the art to more readily understand the properties and advantages of the dosage forms disclosed. The models and examples are presented by way of illustration, and are not meant to be limiting in any way.

(a) Erosion of Two-Dimensional Elements by Diffusion without Convection

FIGS. 6c and 6d show a non-limiting example of a polymeric element with rectangular cross section (e.g., a sheet or two-dimensional element) 602 and its interface 622 after immersion in an unstirred, infinite dissolution medium 652. The excipient polymer molecules are assumed to diffuse away from the interface faster than the dissolution medium diffuses into the element. Thus after a short wait after immersion, the thickness of the diffuse, semi-dilute layer 642 is (and remains) thin compared with the element thickness or the thickness of the dilute region 652. The dissolution rate (or the disintegration rate) of the element 602 may thus be described by the diffusion of excipient molecules from the element interface into the dilute medium. The initial rate of erosion of the element 602 may be approximated by:

$$\frac{1}{2}\frac{dh}{dt} = -\frac{j_e}{\rho_e} \approx -\frac{c_{e,0}}{\rho_e}\sqrt{\frac{D_e}{\pi t}} \tag{1}$$

Integrating Gives $$h(t) = h_0 - \frac{2c_{e,0}}{\rho_e}\sqrt{\frac{4D_e t}{\pi}} \tag{2}$$

where h(t) is the element's thickness as a function of time, $h_0$ the initial thickness of the element, $j_e$ the flux of the eroding excipient polymer, $\rho_e$ the density of the solid excipient, $c_{e,0}$ the interfacial concentration of the excipient polymer, and $D_e$ the diffusivity of an excipient molecule in the dissolution medium.

By way of example but not by way of limitation, if $h_0=250$ μm, $c_{e,0}=163$ kg/m$^3$, $\rho_e=1150$ kg/m$^3$, $D_e=1.09\times10^{-10}$ m$^2$/s, the element thickness decreases to about 170 μm after the time $t=h_0^2/D_e=9.6$ mins. Thus about 32% of the element are dissolved or disintegrated at this time in this example. By contrast, if the element thickness is increased to 5 mm (a typical thickness of a dosage form) and the other parameters are kept the same, only about 1.6% would be eroded 9.6 minutes after immersion in a still fluid. This percentage is more than an order of magnitude smaller than the corresponding value of a thin element. The advantage of a "thin" element over a "thick" element or dosage form for achieving fast disintegration (and high drug release) rates is thus exemplified.

It would be obvious to a person of ordinary skill in the art that the model presented (and any of the following models) are readily adapted to two-dimensional elements of non-rectangular cross section. Such elements include, but are not limited to two-dimensional elements with elliptical, polygonal, or any other cross section. Furthermore, more examples of models of erosion of a single element in a still dissolution medium would be obvious to a person of ordinary skill in the art. All of them are within the scope of this invention.

(b) Diffusion of Dissolution Fluid into an Element

FIGS. 6e and 6f present another non-limiting example of a polymeric element 604 and its interfacial region 624 after immersion in a dissolution fluid 654 that is of infinite extent and stagnant (not stirred). Now it is assumed that water (or dissolution fluid) diffusion into the excipient polymer is faster than polymer diffusion into the fluid. This is opposite of the previous case. In this model, the thickness of the gel-layer 644 grows with time as dissolution fluid continues to diffuse in. Under Fickian diffusion (see, e.g., J. Crank, "The Mathematics of Diffusion", second edition, Oxford University Press, 1975), the time taken by the dissolution fluid 654 to penetrate the element 604 (i.e., to convert it into a gel) may be estimated as:

$$t_{pen} = \frac{h_0^2}{4D_{eff}} \quad (3)$$

where $D_{eff}$ is an effective diffusivity of physiological/body fluid in the polymeric element under physiological conditions. By way of example but not by way of limitation, if $h_0=250$ μm and $D_{eff}=2\times10^{-10}$ m²/s, by Eq. (3) $t_{pen}=78$ seconds. Conversely, if $h_0$ is increased to 5 mm and $D_{eff}$ remains unchanged, $t_{pen}$ increases to 520 minutes. Thus the penetration time of a "thin" element is much shorter than that of a "thick" element or a "thick" dosage form of the same composition.

More such examples of models of diffusion of dissolution fluid into a single element would be obvious to a person of ordinary skill in the art. All of them are within the scope of this invention.

(c) Disintegration of Penetrated Elements

A penetrated element may be considered a polymeric solution (or dispersion or gel) that has a viscosity greater than the viscosity of the dissolution fluid. If the viscosity of the solution (e.g., a penetrated element, the surface of a penetrated element, etc.) is small enough, and if such external forces applied on the element as gravity, shear, or imbalances in fluid pressure are large enough, the solution may deform or break up into pieces. Thus, in some embodiments a penetrated element or a penetrated surface of an element may disintegrate and dissolve rapidly.

(d) Erosion of Element with Convection

FIG. 6g schematically shows a non-limiting example of a polymeric element that erodes in a stirred medium by convective mass transfer 626. The solid polymeric excipient 606 and the dissolution medium 656 are separated by a gelated interfacial layer 646, 648. The excipient concentration at the outer boundary of the layer is zero. It increases towards the interior and reaches the density of the solid at the inner boundary. The velocity of the dissolution medium 656 is equal to the far-filed velocity, $v_\infty$ far away from the interface. It decreases towards the inner boundary of the interfacial layer, and may be considered zero when the excipient concentration exceeds a critical value. Thus, a "critical" concentration may separate the interfacial layer into a dilute, moving concentration boundary layer 648 of thickness, $\delta_c$, and a concentrated, highly viscous, stagnant layer 646. A reasonable estimate or definition of the critical concentration is the concentration, $c_{e,0}$.

In this model, for an element that erodes from both faces by convection (e.g., in a rotating basket of a USP dissolution apparatus), the erosion rate per eroding face may be approximated by:

$$E = -\frac{1}{2}\frac{dh}{dt} = 0.62\left(\frac{D_e c_{e,0}}{\rho_e}\right)\left(\frac{\mu_l}{D_e \rho_l}\right)^{\frac{1}{3}}\left(\frac{\rho_l \Omega}{\mu_l}\right)^{\frac{1}{2}} \quad (4)$$

where $\rho_l$ is the density and $\mu_l$ the viscosity of the dissolution fluid, and Q is the angular velocity of the rotating basket. The disintegration time of the element of initial thickness $H_0$ eroding from both faces is about:

$$t_E = \frac{h_0}{dh/dt} \quad (5)$$

(It may be noted that in the present non-limiting example, erosion from the sides is not considered because the thickness of an element is smaller than its width or length. Furthermore, we may note that the model may be adapted if the eroding surfaces are not planar.)

By way of example but not by way of limitation, if $c_{e,0}=163$ kg/m³, $D_e=1.09\times10^{-10}$ m²/s, $\rho_e=1150$ kg/m³, $\rho_l=1000$ kg/m³, $\mu_l=0.001$ Pa·s, Q=5.24 rad/s, and $h_0=250$ μm, by Eqs. (4) and (5) the calculated $0.8\times t_E=3.6$ min. By contrast, if $h_0$ is increased to 5 mm, $0.8\times t_E$ is 73 min.

Thus, also in this non-limiting example, the "thin" element disintegrates more than an order of magnitude faster than the "thick" element or the "thick" minimally-porous dosage form. Further details related to convective mass transfer models are given, e.g., in V. G. Levich, "Physicochemical Hydrodynamics", Prentice-Hall, Englewood Cliffs, N.J., 1962; for further details related to the USP dissolution apparatus, see, e.g., The United States Pharmacopeial Convention, USP 39-NF 34. Any more examples of models of element erosion with convection obvious to a person of ordinary skill in the art are all within the scope of this invention.

(e) Dosage Form Disintegration in a Stagnant Medium

Figure 7:
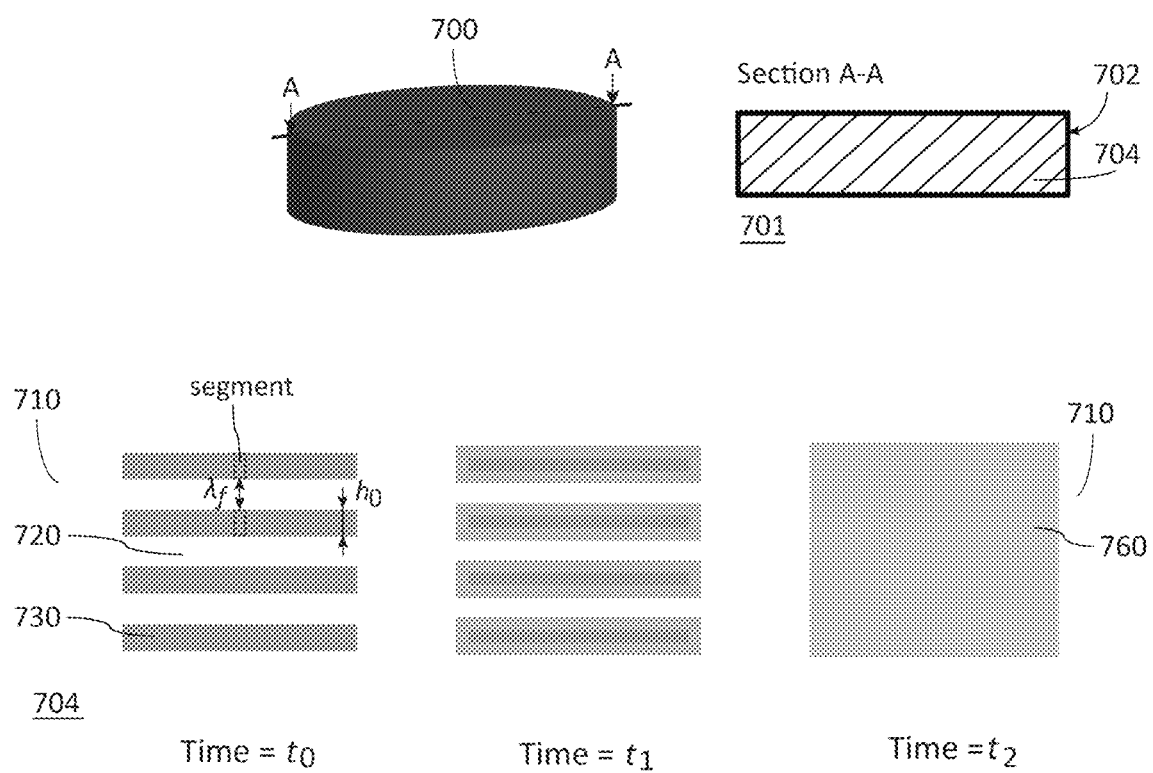
FIG. 7 schematically presents a non-limiting example of the dissolution/disintegration process in a stagnant dissolution fluid by a dosage form herein.

FIG. 7 presents a non-limiting example of the disintegration process of a dosage form 700 in a stagnant dissolution fluid. The dosage form 700 comprises a drug-containing solid 701 having an outer surface 702 and an internal structure 704 contiguous with and terminating at said outer surface 702. The internal structure 704 comprises a three dimensional structural framework of one or more sheets 730. The sheets 730 contain an active ingredient and a polymeric excipient that is absorptive of or soluble in (e.g., erodible by) a dissolution medium. The sheets 730 further comprise segments separated and spaced from adjoining segments by free spacings, $\lambda_f$, which define interconnected free spaces 720 in the drug-containing solid 701.

Upon immersion of the dosage form 700 in a dissolution fluid 710, the interconnected free spaces 720 may be percolated rapidly by the fluid 710 if (a) the interconnected free spaces 720 are (partially or entirely) connected to the outer surface, (b) the content of the interconnected free spaces 720 is partially or entirely removable by the dissolution fluid 710, (c) the free spacing, $\lambda_f$, (e.g., the "free" distance between the one or more elements) is on the sub-micro-, micro-, or meso-scale or greater, and (d) the surface of the sheets is wettable by the dissolution fluid. Thus if the above conditions are satisfied, a sheet 730 in the three dimensional structural framework may be surrounded by the dissolution fluid 710 soon (e.g. in less than about a minute) after immersion of the dosage form 700. It is assumed that this is the case in the non-limiting example described here. The time to percolate part or all of the interconnected free spaces 720 is thus not considered to be rate-determining in dosage form disintegration or drug release.

Subsequent to fluid 710 percolation to the interior of the drug-containing solid 704, the dissolution fluid 710 that surrounds a segment then penetrates into it by diffusion, and the segment may swell and erode. Upon inter-diffusion of the fluid 710 and the polymeric segment, polymer molecules 740 (and gel-layer 750) may spread out. They may intersect with the molecules of adjoining segments at a certain time, $t_1$, after immersion. Then at $t_2$ a polymer-fluid solution 760 is formed. The time $t_2$ to convert the drug-containing solid 704 to such a solution 760 may be estimated by the penetration and erosion times of a single element (or a single segment) 730 in a stagnant fluid 710 (e.g. by Eq. (3)).

If all the interconnected free spaces 720 are percolated by the dissolution fluid 710, the concentration of the excipient polymer, $c_{e,sol}$, in the solution 760 is about:

$$c_{e,sol} = \frac{M_e}{V_e + V_{fs}} \frac{V_0}{V_{sol}} = \frac{\phi_s \phi_e \rho_e}{1 - \phi_s(1-\phi_e)} \frac{V_0}{V_{sol}} \quad (6)$$

where $M_e$ is the mass and $V_e$ the volume of the absorptive/soluble excipient, $V_{fs}$ the volume of the free spaces 720, $V_0$ the initial volume of the dry dosage form, $V_{sol}$ the volume of the solution, $\varphi_s$ the volume fraction of the solid/dry elements in the dry dosage form, $\varphi_e$, the volume fraction of the absorptive/soluble excipient polymer in the dry elements or sheets 730, and $\rho_e$ is the density of the excipient in the dry state.

The solution 760 is dilute and the polymer molecules disentangled if the excipient concentration in the solution 760, $c_{e,sol} \leq c_e^*$, the disentanglement concentration. This is the case if:

$$\phi_s \leq \frac{V_{sol} c_e^*}{V_{sol}(1-\phi_e)c_e^* + V_0 \phi_e \rho_e} \quad (7)$$

Thus if Eq. (7) is satisfied, the polymer concentration in, or the viscosity of, the solution 760 is so small that the solution 760 is dilute or almost dilute. Consequently, the dosage form can be considered disintegrated as soon the single elements or sheets (or segments) 730 are eroded or penetrated. Dosage form 700 disintegration is determined solely by the behavior of a single element or sheet 730, and the interactions between elements may be neglected. Thus for a sheet 730 geometry and properties of the composition as in the non-limiting examples a and b above, the dosage form 700 is disintegrated just a few minutes after immersion. This is well within immediate-release specification, which is one of the most relevant requirements of a typical pharmaceutical dosage form 700.

If the concentration of polymer in the solution 760, $c_{e,sol} \gg c_e^*$, however, the solution 760 may be considered a viscous mass. The viscous mass (or the viscous solution, or the viscous dosage form) then erodes from its exterior surface by diffusion. Thus if the concentration of polymer in (and the viscosity of) the solution 760 are too high, the drug release rate of the dosage form may be reduced substantially. This is detrimental to an immediate-release dosage form. In some embodiments of the invention herein, therefore, the viscosity of the solution 760 formed after inter-diffusion of dissolution fluid 710 and elements 730 is no greater than about 500 Pa·s.

Moreover, in some embodiments the framework or drug-containing solid expands as it transitions to viscous. For further details related to expansion of solid frameworks or drug-containing solids or dosage forms, see, e.g., the U.S. application Ser. No. 16/860,911 titled "Expandable structured dosage form for immediate drug delivery"; the International Application No. PCT/US19/19004 titled "Expanding structured dosage form"; or the International Application No. PCT/US19/52030 titled "Dosage form comprising structured solid-solution framework of sparingly-soluble drug and method for manufacture thereof".

Any more models or examples of the disintegration of a fibrous dosage form in a stagnant fluid obvious to a person of ordinary skill in the art are all within the scope of this invention.

(f) Dosage Form Disintegration in a Stirred Medium

Figure 8:
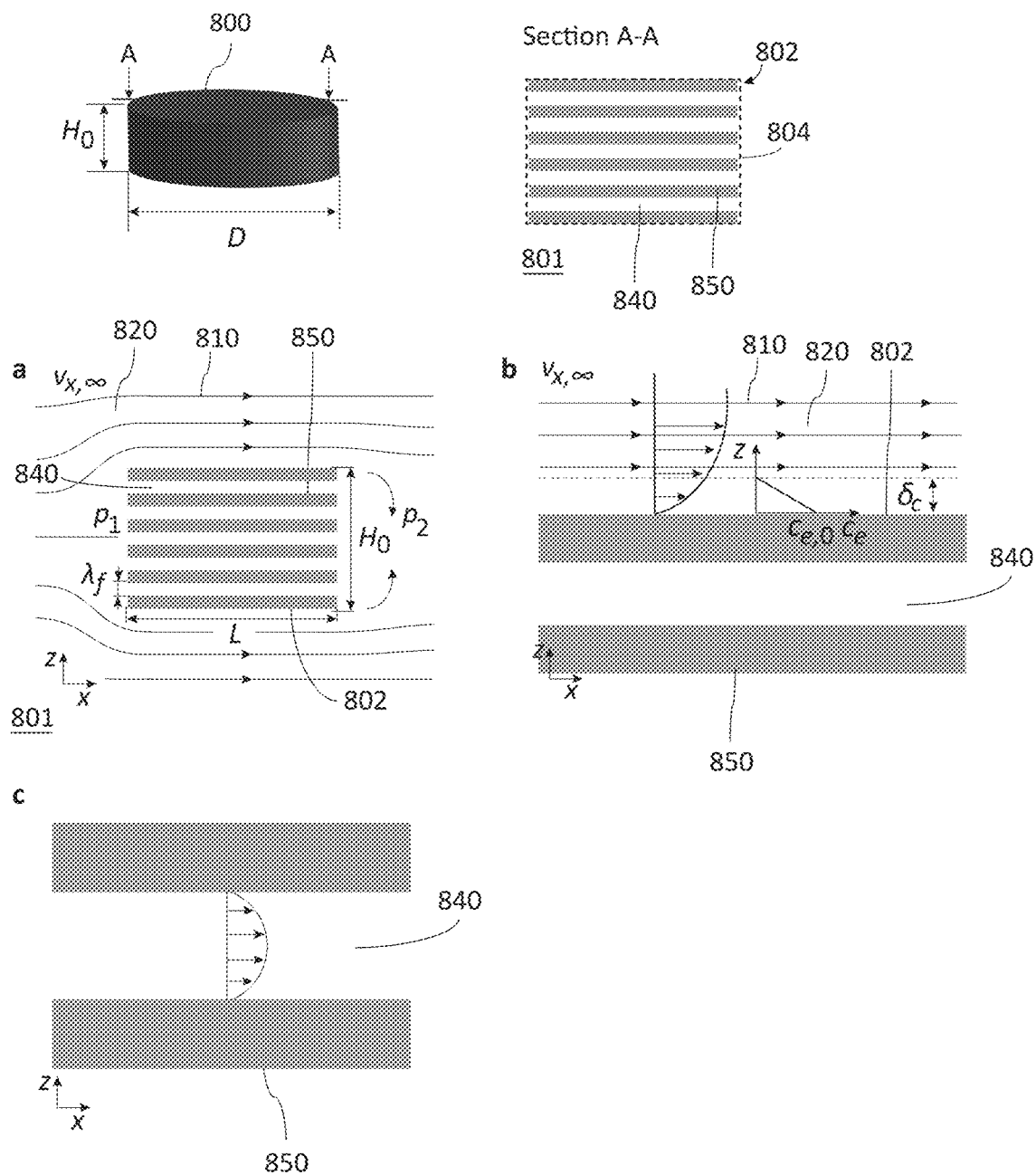
FIG. 8 illustrates non-limiting schematics of fluid flow around and through a dosage form according to this invention.

FIG. 8 presents a non-limiting example of dosage form disintegration in a stirred medium. The dosage form 800 comprises a drug-containing solid 801 having an outer surface 802 and an internal structure 804 contiguous with and terminating at said outer surface 802. The outer surface 802 may comprise a solid, or a liquid, or a gas, and is defined as the plane spanned by the structural elements (e.g., by sheets, fibers, beads, etc.) 850 (or segments thereof) at the surface 802 of the drug-containing solid 801. The internal structure 804 comprises a three dimensional structural framework of elements (e.g., sheets) 850. The elements 850 contain an active ingredient and a water-soluble polymeric excipient. The elements 850 further comprise segments separated and spaced from adjoining segments by free spacings, $\lambda_f$, which define one or more free spaces 840 in the drug-containing solid 801.

Upon immersion in a stirred fluid with far-field velocity, $v_{x,\infty}$, streamlines 810 develop around the dosage form 800 as shown schematically in FIG. 8a. The fluid velocity near the surface 802 is far greater than that in the interior 840. As a result, the erosion rate is greatest at the surface 802. For a case as shown schematically in FIG. 8b the erosion rate of the surface 802 may be approximated by Eq. (4). Using the same parameter values as in section d above, if 10 elements are to be eroded sequentially, the time to erode 80 percent of a dosage form 800 is: $t_{dis} \approx 10 \times 3.7 = 37$ min. This is, however, longer than the required disintegration time of a typical immediate-release dosage form.

Unlike the sequential layer-by-layer removal of material from the surface 802, material removal in the interior 840 of the dosage form is a parallel process because all the elements 850 (e.g. the elements of the internal structure) erode simultaneously. For a velocity profile in the free spaces (or pores) as shown in FIG. 8c, the average fluid velocity in the free spaces, $\bar{v}_x$, may be approximated by:

$$\bar{v}_x = \frac{1}{3} \frac{\Delta p \lambda_f^2}{\mu_l L} \quad (8)$$

where $\Delta p$ is the pressure drop across the channel (or across the dosage form), $\lambda_f$ the free spacing between the elements, $\mu_l$ the viscosity of the liquid dissolution fluid, and L the channel length.

The pressure drop across the dosage form 800 may be estimated from fluid flow outside the dosage form 800 as:

$$\Delta p \approx 0.5 \rho_l v_{x,\infty}^2 \quad (9)$$

Thus the average velocity of the fluid through the internal structure, $\bar{v}_x$, may be estimated as:

$$\bar{v}_x \approx \frac{1}{6} \frac{\rho_l v_{x,\infty}^2 \lambda_f^2}{\mu_l L} \quad (10)$$

For the non-limiting values $v_{x,\infty}=20$ mm/s, $\rho_l=1000$ kg/m³, $\mu_l=0.001$ Pa·s, $\lambda_f=500$ L=10 mm, $\bar{v}_x=1.7$ mm/s. $\bar{v}_x$ is about 12 times smaller than the far-field velocity in this case.

The erosion rate of an element by convection may be estimated by:

$$\frac{1}{2}\frac{dh}{dt} = -\frac{j_e}{\rho_e} \approx \frac{D_e c_{e,0}}{\rho_e \bar{\delta}_c} \quad (11a)$$

where the average concentration boundary layer thickness, $$\bar{\delta}_c \approx 1.56 \left( \frac{D_e \mu_l L^2}{\rho_l v_{x,\infty}^2 \lambda_f} \right)^{1/3} \quad (11b)$$

Thus the erosion time, $$t_E = \frac{h_0}{dh/dt} \approx \frac{h_0 \rho_e}{D_e c_{e,0}} \left( \frac{D_e \mu_l L^2}{\rho_l v_{x,\infty}^2 \lambda_f} \right)^{1/3} \quad (12)$$

Using the non-limiting values $c_{e,0}=163$ kg/m³, $\rho_e=1150$ kg/m³, $D_e=1.09 \times 10^{-10}$ m²/s, $\rho_l=1000$ kg/m³, $\mu_l=0.001$ Pa·s, $v_{x,\infty}=20$ mm/s, and L=10 mm, the time to erode 80 percent of an element, $0.8 \times t_E = 8.3$ min.

The calculated $t_E$ value is well within immediate-release specification, and shorter than the time to disintegrate the dosage form from the exterior surfaces. Thus, even though the velocity through the internal structure 804 is reduced substantially, material removal by simultaneous erosion of elements 850 in the interior may be faster than by sequential erosion from the surface.

It may be noted, however, that even in a stirred medium, if swelling of fibers in the interior is faster than erosion, the fibrous dosage form may disintegrate as described in the non-limiting example e above. In this case, if expansion of the fibrous structure is unconstrained, the disintegration time of the structure is of the order of the penetration time, $t_{pen}$, of a single fiber (see, e.g., Eq. (3)). But if expansion of the structure is constrained, the dosage form structure may form a "viscous mass" after element swelling (for further details, see, e.g., the non-limiting examples (c) and (e) introduced above). Erosion of such a viscous mass would be mostly from the outer surface, which yields a much longer disintegration time than the simultaneous erosion of elements 850 with appreciable fluid flow through the internal structure 804.

Further details related to convective mass transfer models are given, e.g., in R. B. Bird, W. E. Stewart, E. N. Lightfoot, "Transport phenomena", $2^{nd}$ edn., John Wiley & Sons, 2002; and L. Rosenhead, "Laminar boundary layers", Oxford University Press, 1963. Any more models or examples of the disintegration of a fibrous dosage form in a stirred fluid obvious to a person of ordinary skill in the art are all within the scope and spirit of this invention.

(g) Summary of Disintegration Models

The above non-limiting models illustrate the effects of the following design parameters on the disintegration rate of single elements and dosage forms: the geometry of the three dimensional structural framework, the solubility of the excipient in the dissolution medium (e.g., the "interfacial concentration" or "critical concentration" or "$c_{e,0}$"), the diffusivity of the excipient in the dissolution medium, the diffusivity of the medium in the excipient, the fractions of the individual components in the elements, and the disentanglement concentration of the excipient. All these parameters can be deterministically controlled.

Furthermore, the models illustrate that the disclosed dosage forms can be so designed that the length-scale of the disintegration-rate-determining mass transfer step is decreased from the thickness of the dosage form to the thickness (or half-thickness) of the elements. As a result, the disclosed dosage forms can be designed to deliver drug at least an order of magnitude faster than the corresponding non-porous solid forms.

Dosage Form Design Features

In view of the theoretical models and considerations above, which are suggestive and approximate rather than exact, the design and embodiments of the dosage forms disclosed herein comprise the following.

The pharmaceutical dosage forms disclosed herein comprise a drug-containing solid having an outer surface and an internal structure contiguous with and terminating at said outer surface. The internal structure comprises a three dimensional structural framework of one or more two-dimensional elements. The two-dimensional elements comprise at least one active ingredient, and in some cases also at least one excipient. The two-dimensional elements further comprise segments separated and spaced from adjoining segments by free spacings, which define one or more free spaces in the drug-containing solid.

In some embodiments, moreover, dissolution fluid may only percolate into or flow through the interior of the structure (e.g., into at least one free space or into the free spaces) if the drug-containing solid comprises at least a continuous channel or free space having at least two openings in contact with said fluid. The more accessible and the greater the free space is, the more uniformly may the structure be percolated by the dissolution fluid. Uniform percolation and/or flow through the structure is desirable in the invention herein.

Thus, in the invention herein a plurality of adjacent free spaces combine to define one or more interconnected free spaces (e.g., free spaces that are "contiguous" or "in direct contact" or "merged" or "without any wall in between") forming an open pore network that extends over a length at least half the thickness of the drug-containing solid. This includes, but is not limited to a plurality of adjacent free spaces combining to define one or more interconnected free spaces forming an open pore network that extends over a length at least two thirds the thickness of the drug-containing solid, or over a length at least equal to the thickness of the drug-containing solid, or over a length at least equal to the side length of the drug-containing solid, or over a length and width at least equal to half the thickness of the drug-containing solid, or over a length and width at least equal to the thickness of the drug-containing solid, or over a length, width, and thickness at least equal to half the thickness of the drug-containing solid, or over the entire length, width, and thickness of the drug-containing solid.

Moreover, in some embodiments one or more free spaces combine to form a channel having a cross section extending axially along its length from a first end to a second end. The length of said channel may be greater than half the thickness of the drug-containing solid. This includes, but is not limited to a channel having a cross section extending axially along its length from a first end to a second end and having a length at least equal to the thickness of the drug-containing solid, or at least equal to the width of the drug-containing solid, or at least equal to the length of the drug-containing solid. In some embodiments, furthermore, the channel bifurcates into at least one other end (e.g., at least two other ends or at least three other ends or at least four other ends or at least five other ends or at least six other ends), and wherein the length of the channel from the first end to one or more other ends is greater than half the thickness of the drug-containing solid. The cross section of said one or more channels may be greater than 5 µm×5 µm along the length of said one or more channels. This includes, but is not limited to a cross section of said one or more channels greater than 10 µm×10 µm along the length of said one or more channels, or a cross section of said one or more channels greater than 15 µm×15 µm along the length of said one or more channels, or a cross section of said one or more channels greater than 20 µm×20 µm along the length of said one or more channels.

Also, in some embodiments an open pore network comprises or occupies at least 30 percent (e.g., at least 40 percent, or at least 50 percent, or at least 60 percent, or at least 70 percent, or at least 80 percent, or 100 percent) of the free space of the drug-containing solid. In other words, in some embodiments at least 30 percent (e.g., at least 40 percent, or at least 50 percent, or at least 60 percent, or at least 70 percent, or at least 80 percent, or 100 percent) of the free space of the drug-containing solid are part of the same open pore network.

In preferred embodiments, all free spaces are interconnected forming a continuous, single open pore network. In the invention herein, if all free spaces of a drug-containing solid are interconnected the free space of said drug-containing solid is also referred to as "contiguous". In drug-containing solids with contiguous free space, no walls (e.g., walls comprising the three dimensional structural framework of elements) must be ruptured to obtain an interconnected cluster of free space (e.g., an open channel of free space) from a point in the free space to another point (or to any point) in the free space within the internal structure. The entire free space or essentially all free spaces is/are connected.

Moreover, for achieving rapid percolation of dissolution fluid into the free spaces, in some embodiments a "free spacing", $\lambda_f$, (e.g., a "free" distance between adjoining (i.e., neighboring) elements or adjoining segments) is such that the percolation time of physiological/body fluid into one or more interconnected free spaces of the dosage form is no greater than 900 seconds under physiological conditions. This includes, but is not limited to percolation times no greater than 700 seconds, no greater than 500 seconds, no greater than 300 seconds, no greater than 100 seconds, no greater than 50 seconds, or no greater than 10 seconds, or no greater than 5 seconds under physiological conditions. The pressure of the physiological/body fluid at different positions of the interconnected free spaces may assume different values during fluid percolation.

Figure 9:
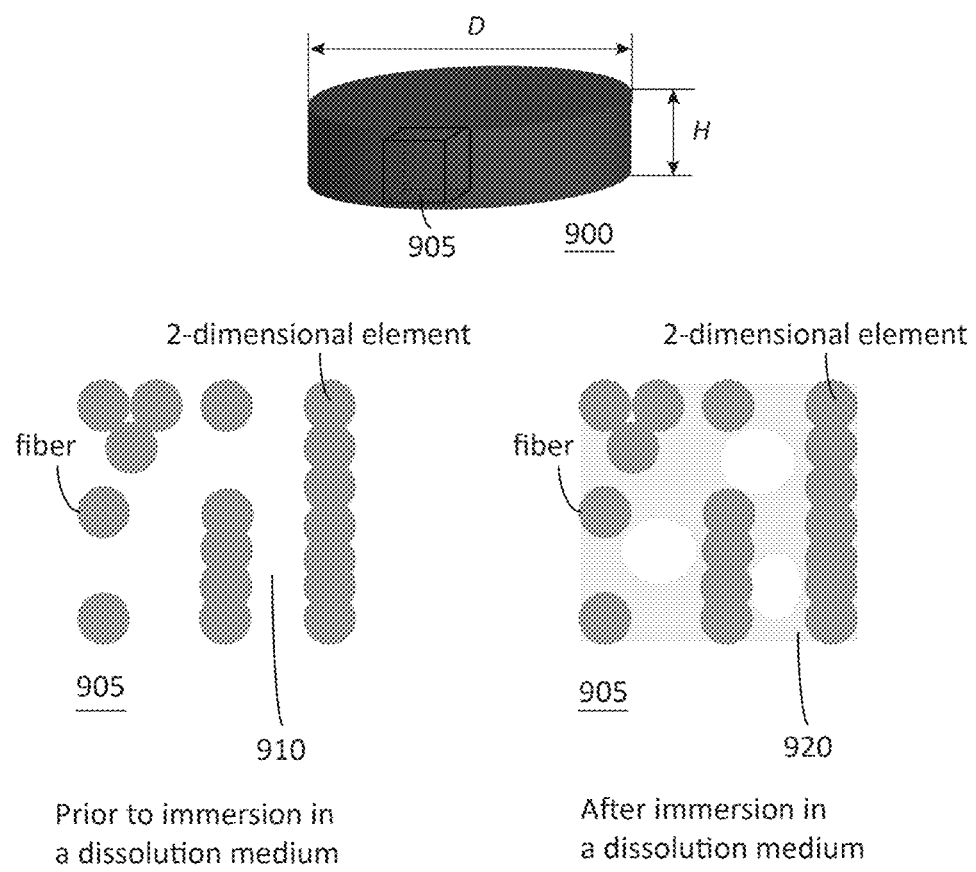
FIG. 9 presents a non-limiting example of dissolution fluid percolation into an interconnected free space.

By way of example but not by way of limitation, the percolation time into one or more interconnected free spaces of the dosage form may be determined as follows (FIG. 9). First a volume 905 of the dosage form 900 may be identified that contains one or more interconnected free spaces 910. Then the volume of the interconnected free spaces 910 in said volume of the dosage form 905 may be determined. Then said volume of the dosage form 905 may be immersed in a dissolution medium. Then the volume of dissolution medium 920 that percolated into the volume of the interconnected free spaces 910 of said volume of the dosage form 905 may be determined. As soon as the volume of dissolution medium 920 that percolated into the volume of the interconnected free spaces 910 of said volume of the dosage form 905 is greater than 20 percent (e.g., greater than 30 percent, or greater than 40 percent, or greater than 60 percent) of the initial volume of the interconnected free spaces 910, the volume of the interconnected free spaces 910 of said volume of the dosage form 905 may be considered percolated.

Also, in some embodiments, the effective free spacing, $\lambda_{f,e}$, on average is greater than 0.1 µm. This includes, but is not limited to an average $\lambda_{f,e}$ greater than 0.25 µm, or greater than 0.5 µm, or greater than 1 µm, or greater than 2 µm, or greater than 5 µm, or greater than 7 µm, or greater than 10 µm, or greater than 15 µm, or greater than 20 µm, or greater than 25 µm, or greater than 30 µm, or greater than 40 µm, or greater than 50 µm, or in the ranges of 0.1 µm-5 mm, 0.1 µm-3 mm, 0.25 µm-5 mm, 0.5 µm-5 mm, 0.25 µm-3 mm, 0.1 µm-2.5 mm, 0.25 µm-2 mm, 1 µm-4 mm, 5 µm-4 mm, 10 µm-4 mm, 15 µm-4 mm, 20 µm-4 mm, 30 µm-4 mm, 40 µm-4 mm, 50 µm-4 mm, or 1 µm-2 mm. The "effective free spacing" between adjoining segments is defined as the maximum diameter of a sphere that fits in the corresponding free space considering the elements as rigid, fixed bodies. The diameter of such spheres may be estimated from 2-d images of the microstructure. Such 2-d images may be obtained from scanning electron micrographs of the cross section of the dosage form. The greatest circles that fit in the free spaces of the microstructure may be drawn on the scanning electron micrograph (e.g., the 2-d image) and the area-based average diameter of the circles (e.g., the average effective free spacing) may be calculated.

Figure 10:
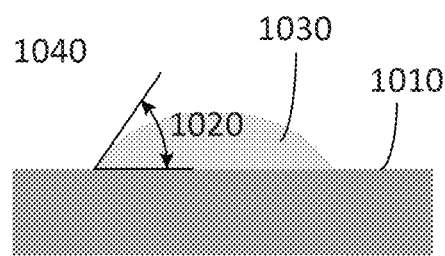
FIG. 10 illustrates a schematic of the contact angle of a fluid droplet on a surface.

Furthermore, in some embodiments at least one of the one or more excipients is wettable by a physiological/body fluid under physiological conditions. In the context of this work, a solid surface 1010 is wettable by a fluid if the contact angle 1020 of a fluid droplet 1030 on the solid surface 1010 exposed to air 1040 is no more than 90 degrees (FIG. 10). In some embodiments, the contact angle may not be stationary. In this case, in the invention herein a solid surface is wettable by a fluid if the contact angle 1020 of a fluid droplet 1030 on the solid surface 1010 exposed to air 1040 is no more than 90 degrees at least 30-500 seconds after the droplet 1030 has been deposited on the surface.

If the two-dimensional elements are parallel to each other, the free spaces between the elements or segments may be intrinsically connected to the outer surface of the dosage form. But if some segments or two-dimensional elements are curved or arranged at an angle to each other, closed cells defining one or more free spaces within the three dimensional structural framework of elements may exist. In a closed individual cell or a closed cluster of cells, the free space is entirely surrounded (i.e., enclosed) by solid walls. In some embodiments, a solid wall, or a fraction thereof, is defined by at least one segment of a two-dimensional drug-containing element.

Figure 11:
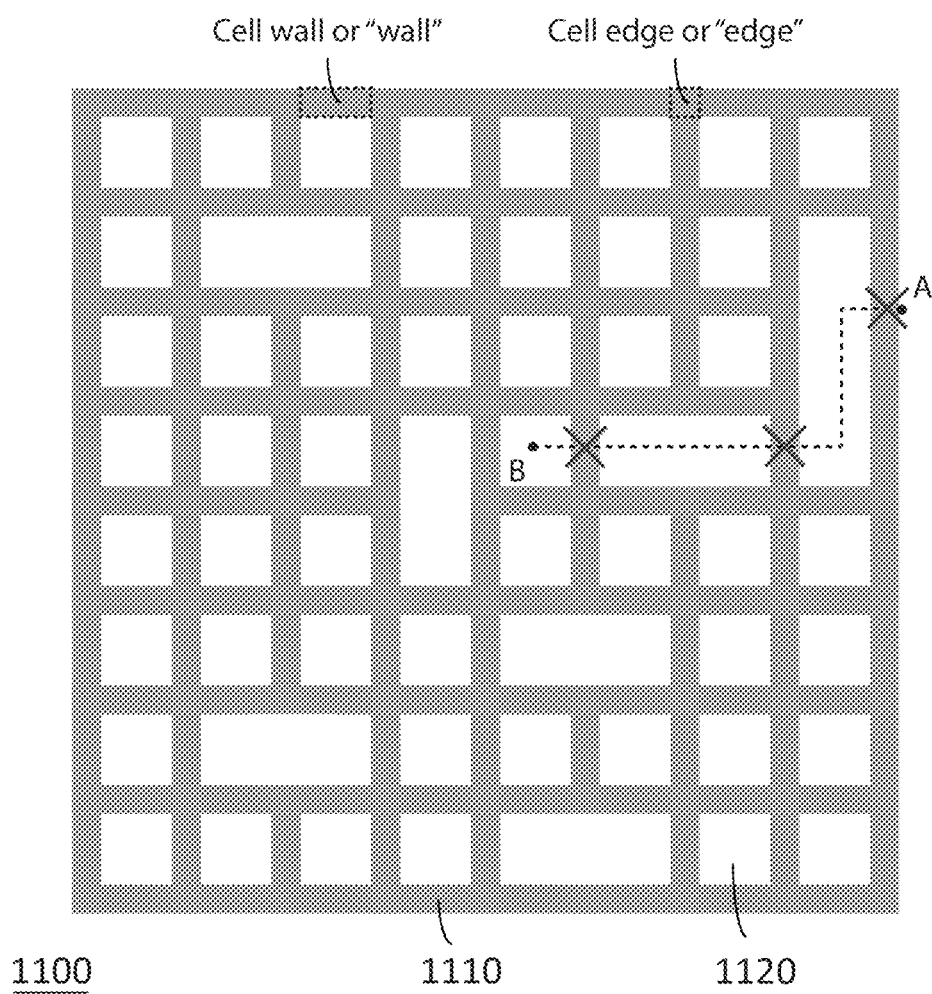
FIG. 11 depicts a non-limiting schematic diagram of the microstructure of solid dosage forms to illustrate the number of walls that must be ruptured to obtain an interconnected cluster of free space that extends from the outer surface of the drug-containing solid to a point in the interior.

In some embodiments disclosed herein, the following holds. An interconnected, continuous cluster of free space that extends from the outer surface of the drug-containing solid to a given point in the internal structure is obtained if no more than 0 to 12 walls are ruptured (e.g., walls of drug-containing solid enclosing free space are opened or removed). This includes, but is not limited to 0-11, 0-10, 0-9, 0-8, 0-7, 0-6, 0-5, 0-4, or zero walls that must be ruptured to obtain an interconnected cluster of free space that extends from the outer surface to a given point in the internal structure. In FIG. 11, a 2-d example without limitation 1100 is presented that shows 3 walls 1110 to be ruptured for obtaining an interconnected cluster of free space 1120 from point A to point B. For achieving rapid release of drug, the free space of the dosage form is preferably connected to the outer surface. In this case, zero walls must be ruptured to obtain an interconnected cluster of free space that extends from the outer surface to a given point in the internal structure.

For achieving a specific surface area (i.e., surface area-to-volume ratio) large enough to guarantee rapid disintegration of an element, in some embodiments the one or more two-dimensional structural elements have an average thickness, $h_0$, no greater than 2.5 mm. This includes, but is not limited to $h_0$ no greater than 2 mm, or no greater than 1.5 mm. It may be noted, however, that if the one or more elements are very thin and tightly packed, the spacing between the segments and elements can be very small, too. This may limit the rate at which dissolution fluid can percolate into or flow through the internal structure upon immersion in a dissolution fluid. Thus, in some embodiments the one or more two-dimensional elements have an average thickness, $h_0$, in the ranges of 0.1 μm-2.5 mm, 0.5 μm-2.5 mm, 1 μm-2.5 mm, 1.75 μm-2.5 mm, 2.5 μm-2.5 mm, 2.5 μm-2 mm, 5 μm-2 mm, 10 μm-2 mm, 15 μm-2.5 mm, 20 μm-2.5 mm, 30 μm-2.5 mm, or 40 μm-2.5 mm. We may further note that the average thickness of the two-dimensional elements, $h_0$, can be greater than 2.5 mm in dosage forms that release drug over longer periods of time (e.g., in a time greater than about 25-45 minutes).

Figure 12:
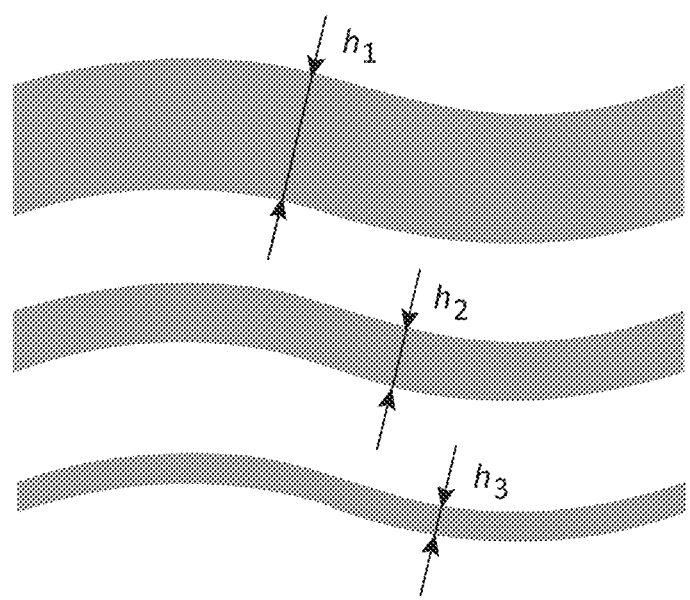
FIG. 12 presents three two-dimensional elements or sheets of different thickness.

The thickness of a two-dimensional element, h, may be considered the smallest dimension of said element (i.e., h≤w and h≤l, where h, w and l are the thickness, width and length of the element, respectively). The average thickness, $h_0$, is the average of the thickness along the length and width of the one or more two-dimensional elements in the internal structure. By way of example but not by way of limitation, FIG. 12 presents three elements of equal length and width but of different thicknesses. In this non-limiting example, the average thickness, $h_0=(h_1+h_2+h_3)/3$. Both the average thickness, $h_0$, and the thickness of a specific element at a specific position, h, may, for example, be derived from scanning electron micrographs of the cross section of the dosage form.

Moreover, if the dosage form further comprises one or more 0-dimensional or 1-dimensional structural elements, the average thickness of the 0D-elements or 1D-elements may be no greater than 2.5 mm in some embodiments disclosed herein. By way of example but not by way of limitation, this includes an average thickness of 0D-elements or 1D-elements no greater than 2 mm, or in the ranges of 0.1 μm-2.5 mm, 0.25 μm-2.5 mm, 0.5 μm-2.5 mm, 2 μm-2.5 mm, 2.5 μm-2 mm, 1 μm-2 mm, 0.5 μm-1.5 mm, or 2 μm-2 mm. The average thickness of a one-dimensional structural element is referred to as the average of the thickness along the length of the element. The average thickness of a zero-dimensional structural element is referred to as the thickness of the element (e.g., the smallest dimension of the element).

Also, we may note that the cross section of a 2D-element (and the cross sections of a 0D-element or 1D-element, too) may assume any shape. Thus, by way of example but not by way of limitation, the cross section may be polygonal, ellipsoidal, circular, rectangular, combinations thereof, and so on. Furthermore, the cross section of a 2D, 1D, or 0D-element may vary along the length of said element.

The dosage form properties (e.g., the uniformity of fluid percolation into the drug-containing solid, the uniformity of dosage form expansion, the drug release rate. etc.) can be optimized if the microstructural parameters are precisely controlled. In the invention herein, the terms "precisely controlled" and "ordered" or "orderly arranged" and "regular" are used interchangeably. A variable or a parameter (e.g., the contact width, the element thickness, the spacing between elements, etc.) is precisely controlled if it is deterministic and not stochastic (or random). A variable or parameter may be deterministic if, upon multiple repetitions of a step that includes said variable (e.g., if multiple dosage forms are produced under identical or almost identical conditions), the standard deviation of the values of said variable is smaller than the average value. This includes, but is not limited to a standard deviation of the values of said variable smaller than half the average value, or smaller than one third of the average value, or smaller than a quarter of the average value, or smaller than one fifth or the average value, or smaller than one sixth, or smaller than one seventh, or smaller than one eight, or smaller than one ninth, or smaller than one tenth, or smaller than 1/12, or smaller than 1/15, or smaller than 1/20, or smaller than 1/25 of the average value of said variable, or smaller than 1/30 of the average value of said variable.

A two-dimensional element or a segment in the three dimensional structural framework of one or more two-dimensional elements may, for example, be defined by its position (e.g., the position of its center of mass, the central plane of the element, etc.) relative to a reference point or frame. (In the invention herein, a reference frame may be understood as a reference coordinate system.) The reference point or the origin and orientation of the reference frame may be specified on the outer surface or within the internal structure of the drug containing solid.

In some embodiments of the invention herein, therefore, the position of at least one two-dimensional element or at least one segment in the internal structure is precisely controlled. Such embodiments include, but are not limited to internal structures wherein the position of a fraction of the elements or segments that make up the three dimensional structural framework of one or more elements is precisely controlled. The volume fraction of elements or segments (with respect to the total volume of elements or segments that make up the three dimensional structural framework of one or more elements) of which the position is precisely controlled can be greater than 0.1, or greater than 0.3, or greater than 0.5, or greater than 0.7, or greater than 0.9.

In some embodiments, furthermore, at least one spacing between segments, λ, and/or at least one free spacing between segments, and/or at least one thickness of a segment or element, h, is/are precisely (or deterministically) controlled. Thus, in some embodiments herein, if an element or segment is produced multiple times under identical conditions, the standard deviation of the thickness of said element or segment is less than the average value of said element's thickness. Similarly, if an inter-element or inter-segment spacing is produced multiple times under identical conditions, the standard deviation of said inter-element or inter-segment spacing is less than the average value in certain embodiments of the invention herein. It may be noted that the inter-element or inter-segment spacing may change along the length or width of said element or segment. Similarly, also the thickness of an element or a segment may change along its length or width.

A non-limiting example of a three dimensional structural framework of one or more elements wherein the position of a large fraction (or all) of the elements, the inter-element spacing, and the element thickness are controlled (or precisely controlled) is an ordered structure. Non-limiting schematics of ordered structures are shown in FIG. 1, FIG. 2, FIG. 3, FIGS. 4a-4e, and FIG. 5. The advantage of ordered structures over disordered or random structures is that the microstructure (e.g., the geometry of the free spaces, etc.) and the properties (e.g., the drug release rate by the structure) can be better controlled.

Typically, the volume fraction of two-dimensional structural elements in the dosage form is no greater than 0.98. In other non-limiting examples, the volume fraction of elements in the dosage form is no greater than 0.95, or no greater than 0.93, or no greater than 0.9. In most cases, it is in the range 0.1-0.9, depending on how the one or more elements are arranged. A small volume fraction of elements is desirable to fill small amounts of drug in a comparable large volume (e.g., if the dosage form is used for delivery of a highly potent drug with a drug dose of just a few milligrams or less). On the contrary, a large volume fraction of elements is desirable to fill large amounts of drug in a small volume (e.g., if the dosage form is used for delivery of a low potency drug or delivery of multiple active ingredients with a total drug dose of several 100 mg or more).

For achieving rapid erosion of elements after contact with physiological/body fluids, in some embodiments the two-dimensional elements include at least one excipient that has a solubility greater than 0.1 g/l in physiological/body fluids under physiological conditions. This includes, but is not limited to a solubility by at least one excipient in a physiological/body fluid greater than 0.5 g/l, or greater than 1 g/l, or greater than 5 g/l, or greater than 10 g/l, or greater than 20 g/l, or greater than 30 g/l, or greater than 50 g/l, or greater than 70 g/l, or greater than 100 g/l. Furthermore, the diffusivity of a dissolved excipient molecule in a physiological/body fluid may be greater than $1 \times 10^{-12}$ m$^2$/s under physiological conditions. This includes, but is not limited to a diffusivity of a dissolved excipient molecule in a physiological/body fluid greater than $2 \times 10^{-12}$ m$^2$/s, greater than $4 \times 10^{-12}$ m$^2$/s, greater than $6 \times 10^{-12}$ m$^2$/s, greater than $8 \times 10^{-12}$ m$^2$/s, or greater than $1 \times 10^{-11}$ m$^2$/s under physiological conditions. The volume fraction of soluble excipient in the excipient (e.g., the excipient in its totality or all the volume of the one or more excipients in the one or more fibers) may be greater than 0.02. This includes, but is not limited to volume fractions of the soluble excipient in the excipient greater than 0.04, greater than 0.06, greater than 0.08, or greater than 0.1.

In polymers that form viscous solutions when combined with a dissolution medium, the 'solubility' in the context of this invention is the polymer concentration in physiological/body fluid at which the average shear viscosity of the polymer-physiological/body fluid solution is 5 Pa·s in the shear rate range 1-100 l/s under physiological conditions. The pH value of the physiological/body fluid may thereby be adjusted to the specific physiological condition of interest. By contrast, the solubility of a material that does not form a viscous solution when combined with a dissolution medium is the maximum amount of said material dissolved in a given volume of dissolution medium at equilibrium divided by said volume of the medium. It may, for example, be determined by optical methods.

Furthermore, in some embodiments the one or more elements include at least one excipient that is absorptive of a physiological/body fluid. The effective diffusivity of physiological/body fluid in an absorptive excipient (and/or an element) may be greater than $0.5 \times 10^{-11}$ m$^2$/s under physiological conditions. In other examples without limitation, the effective diffusivity of physiological/body fluid in an absorptive excipient (and/or an element) may be greater than $1 \times 10^{-11}$ m$^2$/s, greater than $3 \times 10^{-11}$ m$^2$/s, greater than $6 \times 10^{-11}$ m$^2$/s, or greater than $8 \times 10^{-11}$ m$^2$/s under physiological conditions.

Alternatively, (e.g., for absorptive excipients where diffusion of physiological/body fluid to the interior is not Fickian) a rate of penetration may be specified. In some embodiments, the rate of penetration of a physiological/body fluid into a solid, absorptive excipient (and/or an element) is greater than an average thickness of the one or more elements in the internal structure divided by 3600 seconds (i.e., $h_0/3600$ μm/s). In other examples without limitation, rate of penetration may be greater than $h_0/1800$ μm/s, greater than $h_0/1200$ μm/s, greater than $h_0/800$ μm/s, or greater than $h_0/600$ μm/s.

For determining the effective diffusivity (and/or the rate of penetration) of dissolution medium in a solid, absorptive excipient (and/or an element) the following procedure may be applied. An element (e.g. an element of the dosage form structure or an element that just consists of the absorptive excipient) may be fixed at two ends and placed in a still dissolution medium at 37° C. The time $t_1$ for the element to break apart or deform substantially may be recorded. (By way of example but not by way of limitation, a deformation of an element may be considered substantial if either the length, width, or thickness of the element differs by more than 10 to 20 percent from its initial value. In elements with weight fraction, $w_e$, or volume fraction, $\varphi_e$, of absorptive/swellable excipient smaller than 0.4, a deformation of an element may be considered substantial if either the length, width, or thickness of the element differs by more than $25 \times \varphi_e$ percent or $25 \times w_e$ percent from its initial value.) The effective diffusivity, $D_{eff}$, may then be determined according to $D_{eff} = h_0^2/4t_1$ where $h_0$ is the initial element thickness (e.g., the thickness of the dry element). Similarly, the rate of penetration of a physiological/body fluid into the element is equal to $h_0/2t_1$.

The effective diffusivity of dissolution medium in or the average velocity at which the fluid front advances (i.e., the rate of penetration of a physiological/body fluid) into a solid, absorptive excipient (or an element) may also be determined by spectral methods. By way of example but not by way of limitation, one side of an element may be exposed to the dissolution medium. On the other side of the element, the concentration of dissolution medium may be monitored. As soon as the monitored concentration of dissolution medium raises substantially (e.g., as soon as the concentration of water or dissolution fluid in the absorptive/swellable excipient on the monitored surface is greater than twice the concentration of water or dissolution fluid in the absorptive/swellable excipient of the initial solid element), the element is penetrated. The time $t_1$ to penetrate the element may be recorded and the effective diffusivity and rate of penetration calculated as detailed in the previous paragraph. Spectral methods are suited for materials that have some mechanical strength (i.e., increased viscosity) when they are penetrated by the dissolution fluid. They are also suited for materials (or elements) where the deformation of the element upon penetration of dissolution fluid is small.

In some embodiments, at least one excipient of the drug-containing solid transitions from solid to a fluidic or gel consistency solution upon being solvated with a volume of physiological/body fluid equal to the volume of the one or more free spaces of the drug-containing solid (or dosage form). To ensure that the disintegration rate of such a drug-containing solid is of the order of the disintegration rate of a single element (e.g., to avoid that the drug-containing solid forms a viscous mass upon immersion in a dissolution medium that erodes slowly from its outer surfaces), the viscosity of said solution is no greater than 500 Pa·s. In other words, a solution comprising the weight of soluble/absorptive excipient in the drug-containing solid and a volume of physiological/body fluid equal to the volume of the free spaces of the drug-containing solid (specifically the volume of the free spaces that are removable by the dissolution fluid), has a viscosity no greater than 500 Pa·s. This includes, but is not limited to a viscosity of said solution less than 400 Pa·s, less than 300 Pa·s, less than 200 Pa·s, less than 100 Pa·s, less than 50 Pa·s, less than 25 Pa·s, or less than 10 Pa·s. In the context of this work, the viscosity of a solution is the average shear viscosity of the solution in the shear rate range 1-100 l/s under physiological conditions.

Non-limiting examples of excipients that if used at the right quantities satisfy some or all of the above requirements include polyethylene glycol (PEG), polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, hydroxypropyl methylcellulose), starch, polylactide-co-glycolide, polyvinyl caprolactam-polyvinyl acetate-polyethylene glycol graft copolymer, pregelatinized starch, lactose, sodium starch glycolate, polyacrylic acid, acrylic acid crosslinked with allyl sucrose or allyl pentaerythritol (e.g., carbopol), or polyols (e.g., lactitol, maltitol, mannitol, isomalt, xylitol, sorbitol, maltodextrin, etc.), among others.

In some embodiments, at least one excipient has a molecular weight (e.g., an average molecular weight) in the range between 0.8 kg/mol and 2000 kg/mol. In some embodiments, moreover, the average molecular weight of an excipient may be in the range 1,000 g/mol to 300,000 g/mol. This includes, but is not limited to an average molecular weight of the excipient in the range 2,000 g/mol to 200,000 g/mol.

The one or more free spaces may be filled with a matter selected from the group comprising solid, liquid, gas (or vacuum), or combinations thereof. If one or more elements (or one or more segments) is/are partially or entirely surrounded by free space, the content of said free space may be removed partially or entirely after contact with dissolution fluid to give the fluid access to the elements. This condition is, for example, satisfied by gases. Examples of biocompatible gases that may fill the free space include air, nitrogen, $CO_2$, argon, oxygen, and nitric oxide, among others.

Liquids that are partially or entirely removed from the structure upon contact with dissolution fluid, and thus may be used to fill the free spaces include, but are not limited to such biocompatible low viscosity fluids as: Polyethylene glycol (PEG) with molecular weight smaller than about 1000 Da (e.g. PEG 400, PEG 300, etc.), Poloxamer 124, 2-Pyrrolidone, Glycerol triacetate (Triacetin), D-alpha tocopheryl polyethylene glycol 1000 succinate (TPGS), Polyoxyl Hydroxystearate, Polyoxyl 15 Hydroxystearate, Castor oil, Polyoxyl castor oil (Polyethoxylated castor oil), Polyoxyl 35 castor oil, Polyoxyl hydrogenated castor oil, Glyceryl monooeleate, Glycerin, Propylene glycol, Propylene carbonate, Propionic acid, Peanut oil, water, Sesame oil, Olive oil, Almond oil, combinations of such (and/or other) liquids with a polymer or any other molecule that dissolves in them, among others.

Non-limiting examples of solids that are removed or dissolved after contact with physiological/body fluid include sugars or polyols, such as Sucrose, Lactose, Maltose, Glucose, Maltodextrin, Mannitol, Maltitol, Isomalt, Lactitol, Xylitol, Sorbitol, among others. Other examples of solids include polymers, such as polyethylene glycol, polyvinyl pyrrolidone, polyvinyl alcohol, among others. Other examples of solids include effervescent agents, such as sodium bicarbonate. The relevant physical properties of a solid that is bonded to a drug-containing fiber are high solubility and diffusivity in physiological/body fluids to ensure its rapid removal after contact with physiological/body fluid. Thus other non-limiting examples of a solid include solid active pharmaceutical ingredients with high solubility and diffusivity, such as Aliskiren. Typically, a solid material should have a solubility in physiological/body fluid under physiological conditions greater than 50 g/l to be removed or dissolved rapidly after contact with dissolution medium. This includes, but is not limited to a solubility greater than 75 g/l, or greater than 100 g/l, or greater than 150 g/l. The diffusivity of the solid material (as dissolved molecule in physiological/body fluid under physiological conditions) should typically be greater than $4\times10^{-12}$ m$^2$/s if the solid material must be dissolved rapidly after contact with dissolution medium. This includes, but is not limited to a diffusivity greater than $6\times10^{-12}$ m$^2$/s, or greater than $8\times10^{-12}$ m$^2$/s, or greater than $1\times10^{-11}$ m$^2$/s.

Furthermore, one or more filler materials such as microcrystalline cellulose or others, one or more sweeteners, one or more taste masking agents, one or more stabilizing agents, one or more preservatives, one or more coloring agents, or any other common or uncommon excipient may be added as excipient to the dosage form.

In some embodiments, a disintegration time of the dosage form (or the drug-containing solid) is no greater than 50 minutes. This includes, but is not limited to a disintegration time no greater than 40 minutes, no greater than 30 minutes, no greater than 25 minutes, no greater than 20 minutes, or no greater than 15 minutes. In the context of this disclosure, the disintegration time is defined as the time required to release 80 percent of the drug content of a representative dosage form structure into a stirred dissolution medium. The released drug may be a solid, such as a solid drug particle, and/or a molecule, such as a dissolved drug molecule. The disintegration test may, for example, be conducted with a USP disintegration apparatus under physiological conditions. (See, e.g. The United States Pharmacopeial Convention, USP 39-NF 34). Another method without limitation to conduct a disintegration test is by a USP basket apparatus (i.e., a USP apparatus 1 as shown in The United States Pharmacopeial Convention, USP 39-NF 34) under physiological conditions (e.g., at a temperature of 37° C. and at a stirring rate or basket rotation rate of 50-150 rpm). In this method, the time to disintegrate 80 percent of the representative dosage form structure after immersion in the stirred dissolution medium may, for example, be determined by visual or other optical methods. It may be noted that if the drug is in molecular form immediately or almost immediately after it is released from the dosage form structure, the disintegration time is about the same as the time to dissolve 80% of the drug content of a representative dosage form structure after immersion in a stirred dissolution medium.

Generally, the dosage form or drug-containing solid herein comprises a continuous, three dimensional skeleton comprising one or more sheets and in some embodiments also one or more fibers or one or more particles or beads. Thus, elements (e.g., sheets, fibers, particles, or beads) may be in contact with other elements. Such contacts may comprise point contacts, line contacts, or plane contacts. A non-limiting example of a point contact is the contact between a sheet and a particle or bead. A non-limiting example of a line contact is the contact between a fiber and a sheet along the length of said fiber. A non-limiting example of a plane contact is the planar contact between two sheets (e.g., the contact between two sheets along the length and width of said sheets). For further information related to point contacts, line contacts, and plane contacts, see, e.g., the International Application No. PCT/US19/52030 titled "Dosage form comprising structured solid-solution framework of sparingly-soluble drug and method for manufacture thereof"; or K. L. Johnson, "Contact mechanics", Cambridge University Press, 1985, including all references cited therein.

In some embodiments, the number of contacts between elements in the three dimensional structural framework is precisely controlled. This is usually the case in regular or ordered structure, and is a preferred embodiment herein.

At the contact zone (e.g., at one or more point contacts or at one or more line contacts, plane contacts, etc.) two elements or segments may be bonded, which is understood herein as "fixed", "joined", "attached", etc. Generally, the bond strength is a fraction of the bulk strength of the contacting elements or segments. Said fraction is typically no greater than 1. This includes but is not limited to a bond strength no greater than 0.8, or no greater than 0.6, or no greater than 0.4, or no greater than 0.2, or no greater than 0.1, or in the ranges 0.001-1, 0.001-0.95, 0.001-0.9, 0.005-1, 0.005-0.95, or 0.01-0.9 times the strength of the bulk of elements or segments. For further information about determining and measuring strength of solid materials, see, e.g., J. M Gere, S. Timoshenko, "Mechanics of materials", fourth edition, PWS Publishing Company, 1997; M. F. Ashby, "Materials selection in mechanical design", fourth edition, Butterworth-Heinemann, 2011; K. L. Johnson, "Contact mechanics", Cambridge University Press, 1985.

In preferred embodiments, bonding between an element or segment and another element or segment is by interdiffusion of molecules between said elements or segments. The bond may then be comparable to a bond obtained by welding or fusing the two elements together.

Thus, in some embodiments, the three dimensional structural framework of one or more elements is a solid forming a continuous structure wherein at least one element or at least one segment of an element is bonded to another element or another segment of an element. This includes, but is not limited to a three dimensional structural framework of one or more elements forming a continuous solid structure wherein at least two elements or at least two segments of an element, or at least three elements or at least three segments of an element, or at least four elements or at least four segments of an element, or at least five elements or at least five segments of an element, are bonded to another element or another segment of an element.

In preferred embodiments, the internal structure of the drug-containing solid comprises stacked layers of sheets that are separated and spaced from adjoining sheets by layers of fibers or particles or beads positioned in between said sheets. In some embodiments, therefore, the internal structure comprises at least two stacked layers of sheets. This includes, but is not limited to at least 3, or at least 4, or at least 5, or at least 6, or at least 7, or at least 8, or 2-5000, or 3-5000, or 4-5000, or 5-5000, or 4-400 stacked layers of sheets. The fibers or particles or beads in between the sheets may further be bonded to said sheets.

As the bonded contacts may provide mechanical support to the three dimensional structural framework of elements, they may also hold up disintegration and dissolution of the structure upon immersion in a dissolution medium. Thus, in some embodiments, a contact width, 2a, between two elements (or two segments) is no greater than 2.5 mm. This includes, but is not limited to a contact width between two elements (or two segments) no greater than 2 mm, or no greater than 1.75 mm, or no greater than 1.5 mm. In other examples without limitation, a contact width, 2a, between two elements (or two segments) may be no greater than 1.1 times the thickness of the contacting elements (or segments) at the position of the contact. This includes, but is not limited to a contact width, 2a, between two elements (or two segments) no greater than 1 time, or no greater 0.8 times, or no greater than 0.6 times the thickness of the contacting elements (or segments) at the position of the contact. Further, in some embodiments, average contact width, 2a, between two elements (or two segments) is no greater than 2.5 mm. This includes, but is not limited to an average contact width between two elements (or two segments) no greater than 2 mm, or no greater than 1.75 mm, or no greater than 1.5 mm.

Moreover, in some embodiments, the contact width of contacts between elements or segments in a dosage form or drug-containing solid or three dimensional structural framework of elements is precisely controlled.

In case the elements are well bonded to each other (or to a solid material that fills the one or more free spaces), the greater of a tensile strength or a yield strength of the assembled dosage form material (e.g., the dosage form or the drug-containing solid) is no less than 0.005 MPa. In other examples without limitation, the greater of a tensile strength or a yield strength of the assembled dosage form material is no less than 0.01 MPa, or no less than 0.015 MPa, or no less than 0.02 MPa, or no less than 0.025 MPa, or no less than 0.04 MPa, or no less than 0.06 MPa, or no less than 0.1 MPa, or no less than 0.25 MPa, or no less than 0.5 MPa or in the ranges 0.01 MPa-100 MPa, 0.02 MPa-100 MPa, 0.05 MPa-100 MPa, 0.1 MPa-100 MPa, 0.2 MPa-100 MPa, or 0.5 MPa-100 MPa.

In some embodiments, the dosage form may be coated. A coating may serve as taste masking agent, protective coating, means of providing color to the dosage form, enteric coating, means of improving the aesthetics of the dosage form, or have any other common or uncommon function of a coating. Moreover, in some non-limiting examples of the invention herein, a coating may be applied on the 2D-elements of the three dimensional structural framework of one ore more 2D-elements.

Also the coating materials include, but are not limited to polyethylene glycol (PEG), polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, butylmethacrylat-(2-dimethylaminoethyl)methacrylat-methyl-mathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, hydroxypropyl methylcellulose), starch, polylactide-co-glycolide, polyvinyl caprolactam-polyvinyl acetate-polyethylene glycol graft copolymer, pregelatinized starch, lactose, sodium starch glycolate, or polyacrylic acid, Sucrose, Lactose, Maltose, Glucose, Maltodextrin, Mannitol, Maltitol, Isomalt, Lactitol, Xylitol, Sorbitol, a sweetener, a coloring agent, a preservative, a stabilizer, a taste masking agent, among others.

Figure 13:
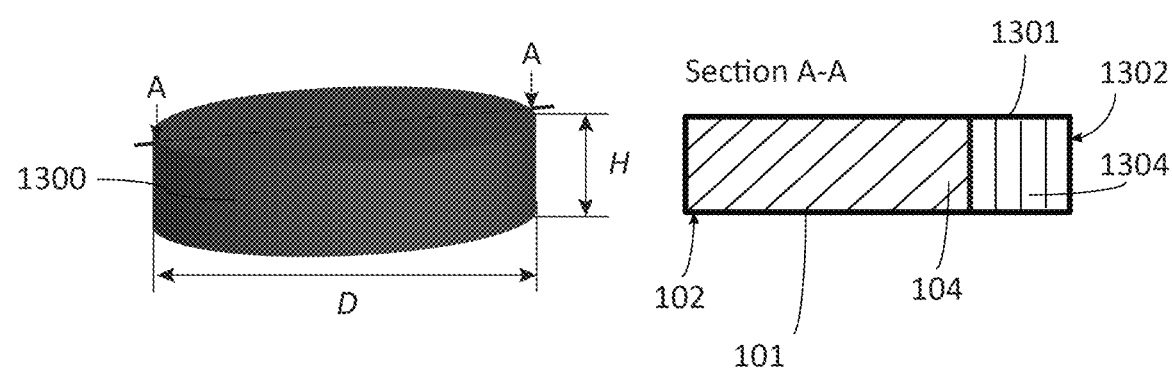
FIG. 13 presents a dosage form comprising at least two drug-containing solids.

In some embodiments, in addition to the drug-containing solid 101, 201, 251, 301, 401 described above, the dosage form 1300 disclosed herein may comprise another drug-containing solid 1301 that contains at least one active ingredient (or one or more other drug-containing solids that contain at least one active ingredient; all such other drug-containing solids are referred to here as "other solid" or "other drug-containing solid"). Said other drug-containing solid 1301 has an outer surface 1302 and internal structure 1304 contiguous with and terminating at said outer surface 1302 as shown in FIG. 13. In some embodiments, 80 percent of the other solid's 1301 drug content is converted to dissolved molecules in a time greater than 60 minutes after immersion of the dosage form in a physiological/body fluid under physiological conditions. In other embodiments, 80 percent of the other solid's 1301 drug content is converted to dissolved molecules in a time no greater than 60 minutes after immersion of the dosage form in a physiological/body fluid under physiological conditions.

In some embodiments, a two-dimensional elements may comprise multiple layers of different materials. This includes, but is not limited to a coating.

EXPERIMENTAL EXAMPLES

The following examples illustrate ways by which the dosage forms may be prepared and analyzed, and will enable one of skill in the art to more readily understand the principle thereof. The examples are presented by way of illustration and are not meant to be limiting in any way.

Example 1: Preparation of Dosage Forms

Figure 14:
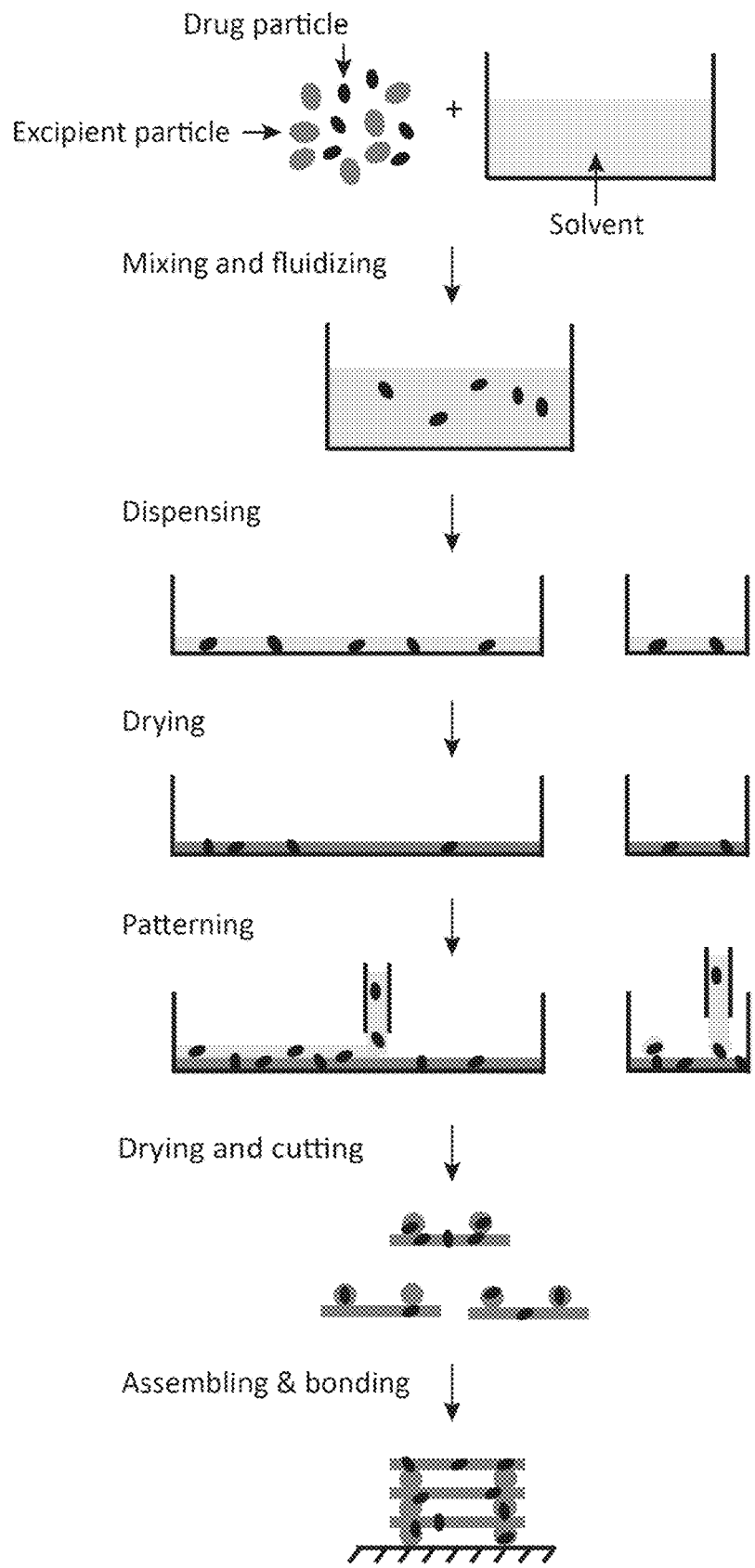
FIG. 14 is a schematic of a non-limiting process to produce the dosage forms disclosed herein.

Dosage forms were prepared as shown schematically in FIG. 14. Drug (acetaminophen) and excipient (polyvinyl alcohol-polyethylene glycol graft copolymer 3:1 of molecular weight 45 kg/mol) particles were first combined and mixed with a solvent (water) to form a liquid dispersion of dissolved excipient, dissolved drug, solvent, and drug particles. The weight fraction of drug in the liquid dispersion was 0.09, the weight fraction of excipient 0.25, and the weight fraction of water 0.66. About 0.35 ml of the dispersion was then dispensed into an open mold with a width of 10 mm and a length of 100 mm. Subsequently, the dispersion was exposed to an air stream at 60° C. for 15 minutes to evaporate the solvent and form a thin film. A fiber pattern was then deposited on the solid film. The composition of the fibers was 0.14 wt % acetaminophen, 0.38 wt % polyvinyl alcohol-polyethylene glycol graft copolymer 3:1 of molecular weight 45 kg/mol and 0.48 wt % water. The radius of the wet fibers was about 250 μm and the inter-fiber spacing was about 6 mm. Finally, the film was cut into square disks of 10 mm side length; the disks (e.g., the elements) were then assembled, bonded to a dosage form structure, and dried. The dosage forms were square disks: 10 mm in side length and about 5 mm in thickness.

Example 2: Dosage Form Microstructures

Figure 15:
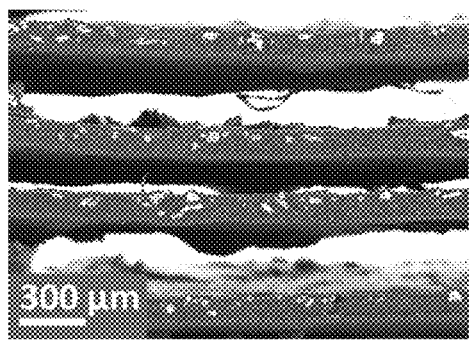
FIG. 15 depicts a scanning electron micrograph of a dosage form according to this invention.

FIG. 15 presents a scanning electron micrograph of the microstructure of a dosage form produced as detailed in the non-limiting experimental example 1. The thickness of the 2D-elements in the dosage form structure was 120±10 μm and the free spacing between the 2D-elements was 285±96

Example 3: Drug Release

Drug release by a dosage form that was prepared as detailed in example 1 was tested using a USP dissolution apparatus 1 (as shown, e.g., in The United States Pharmacopeial Convention, USP 39-NF 34). The apparatus was filled with 900 ml of the dissolution fluid (a 0.05 M phosphate buffer solution with pH 5.8 at a temperature of 37±2° C.). The basket was rotated at 50 rpm. The concentration of dissolved drug in the dissolution fluid was measured versus time by UV absorption at 244 nm using a fiber optic probe. For all the dosage forms, the fraction of drug dissolved increased steadily with time at roughly constant rate until it plateaud out to the final value.

Figure 16:
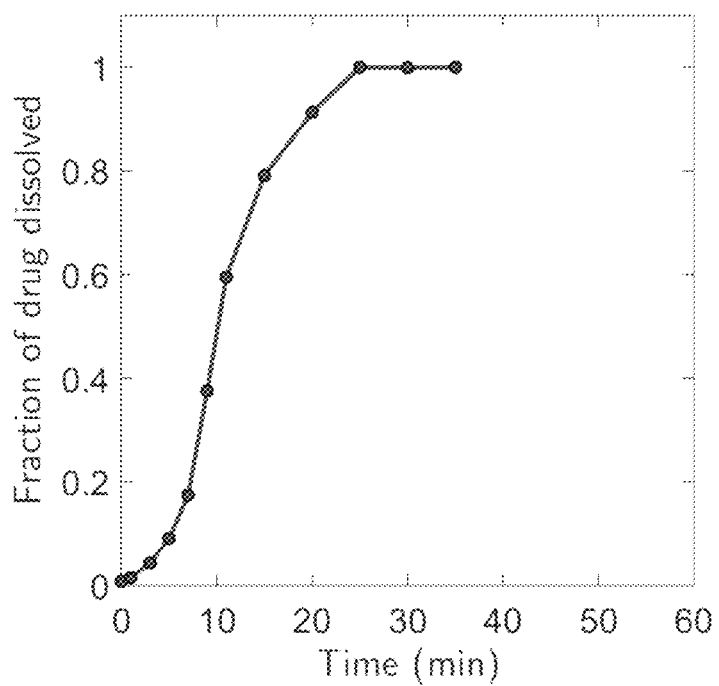
FIG. 16 displays the results of the fraction of drug dissolved versus time of a dosage form according to this invention.

FIG. 16 presents a representative curve of the fraction of drug dissolved versus time of the dosage form prepared as detailed in the non-limiting experimental example 1. The fraction of drug dissolved increased steadily with time and then plateaud out to the final value. The time to dissolve 80% of the drug content, $t_{0.8}$, could thus be readily extracted: it was 15 minutes.

Dosage Form Application Examples

In some embodiments, the amount of active ingredient contained in a dosage form disclosed in this invention is appropriate for administration in a therapeutic regimen that shows a statistically significant probability of achieving a predetermined therapeutic effect when administered to a relevant population. By way of example but not by way of limitation, active ingredients may be selected from the group consisting of acetaminophen, aspirin, caffeine, ibuprofen, an analgesic, an anti-inflammatory agent, an anthelmintic, anti-arrhythmic, antibiotic, anticoagulant, antidepressant, antidiabetic, antiepileptic, antihistamine, antihypertensive, antimuscarinic, antimycobacterial, antineoplastic, immunosuppressant, antithyroid, antiviral, anxiolytic and sedatives, beta-adrenoceptor blocking agents, cardiac inotropic agent, corticosteroid, cough suppressant, diuretic, dopaminergic, immunological agent, lipid regulating agent, muscle relaxant, parasympathomimetic, parathyroid, calcitonin and biphosphonates, prostaglandin, radiopharmaceutical, anti-allergic agent, sympathomimetic, thyroid agent, PDE IV inhibitor, CSBP/RK/p38 inhibitor, or a vasodilator).

In conclusion, this invention discloses a dosage form with predictable structure and drug release behavior. Both can be tailored by well-controllable parameters. This enables faster and more economical pharmaceutical development and manufacture, a greater range of dosage form properties, improved quality of the dosage forms, and more personalized medical treatments.

It is contemplated that a particular feature described either individually or as part of an embodiment in this disclosure can be combined with other individually described features, or parts of other embodiments, even if the other features and embodiments make no mention of the particular feature.

Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

We claim:

1. A pharmaceutical dosage form comprising:
a drug-containing solid having an outer surface and an internal structure contiguous with and terminating at said outer surface;
said internal structure comprising a continuous, three dimensional structural skeleton of one or more stacked sheets, wherein average thickness of said sheets is no greater than 1 mm;
said sheets comprising at least one active ingredient and at least one excipient through their thickness, wherein at least one excipient has a solubility in physiological fluid under physiological conditions no less than 1 g/l;
said sheets further comprising segments separated and spaced from adjoining segments by free spacings, said free spacings defining one or more interconnected free spaces through or across the drug-containing solid; and
one or more interconnected free spaces terminating at said outer surface and filled with at least a gas.

2. The dosage form of claim 1, wherein the internal structure further comprises one or more zero-dimensional elements bonded to and positioned between sheets or segments thereof to separate sheets or segments thereof by free spacings.

3. The dosage form of claim 1, wherein the internal structure further comprises one or more fibers bonded to and positioned between sheets or segments thereof to separate sheets or segments thereof by free spacings.

4. The dosage form of claim 1, wherein at least one element or segment thereof is bonded to another element or segment by interdiffusion of molecules between said elements or segments.

5. The dosage form of claim 1, wherein the free spacing between segments is so that the percolation time of physiological/body fluid into one or more interconnected free spaces of the dosage form is no greater than 900 seconds under physiological conditions.

6. The dosage form of claim 1, wherein the effective free spacing between segments across the one or more interconnected free spaces on average is in the range between 1 μm and 4 mm.

7. The dosage form of claim 1, wherein the spacing between sheets or segments thereof is precisely controlled through or across the drug-containing solid.

8. The dosage form of claim 1, wherein the three dimensional structural skeleton of sheets comprises an ordered structure.

9. The dosage form of claim 1, wherein the thickness of at least one sheet is precisely controlled.

10. The dosage form of claim 1, wherein at least one excipient is wettable by a physiological/body fluid under physiological conditions.

11. The dosage form of claim 1, wherein at least one element or segment thereof is in contact with another element or segment, and wherein the number of contacts between elements or segments thereof within the drug-containing solid is precisely controlled.

12. The dosage form of claim 1, wherein dissolved molecules of the soluble excipient comprise a diffusivity greater than $0.2\times10^{-12}$ m$^2$/s in a physiological/body fluid under physiological conditions.

13. The dosage form of claim 1, wherein at least one excipient is absorptive of a physiological/body fluid, and wherein rate of penetration of the physiological/body fluid into a sheet or said absorptive excipient under physiological conditions is greater than the average thickness of said sheet divided by 3600 seconds.

14. The dosage form of claim 1, wherein at least one excipient is absorptive of a physiological/body fluid, and wherein an effective diffusivity of physiological/body fluid in a sheet or said absorptive excipient is greater than $0.5\times10^{-11}$ m$^2$/s under physiological conditions.

15. The dosage form of claim 1, wherein at least one excipient transitions from solid to a fluidic or gel consistency solution upon contact with a volume of physiological/body fluid equal to the volume of the one or more interconnected free spaces of the drug-containing solid, said solution having a viscosity less than 500 Pa·s under physiological conditions.

16. The dosage form of claim 1, wherein at least one excipient is selected from the group comprising polyethylene glycol (PEG), polyethylene oxide, polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, or butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, or hydroxypropyl methylcellulose), starch, polylactide-co-glycolide, polyvinyl caprolactam-polyvinyl acetate-polyethylene glycol graft copolymer, lactose, starch derivatives (e.g., pregelatinized starch or sodium starch glycolate), chitosan, pectin, polyols (e.g., lactitol, maltitol, mannitol, isomalt), acrylic acid crosslinked with allyl sucrose or allyl pentaerythritol (e.g., carbopol), and polyacrylic acid.

17. The dosage form of claim 1, wherein an interconnected free space is filled with a matter selected from the group comprising gas, liquid, or solid, or combinations thereof, and wherein said matter is partially or entirely removed upon contact with a physiological/body fluid under physiological conditions.

18. The dosage form of claim 17, wherein the gas comprises at least one of air, nitrogen, CO$_2$, argon, or oxygen.

19. The dosage form of claim 1, wherein at least one interconnected free space or open pore network extends over a length at least half the thickness of the drug-containing solid.

20. The dosage form of claim 1, wherein the free space is contiguous.

21. A pharmaceutical dosage form comprising:
a drug-containing solid having an outer surface and an internal structure contiguous with and terminating at said outer surface;
said internal structure comprising a continuous, three dimensional structural framework of one or more sheets, wherein average thickness of said sheets is no greater than 1 mm;
said sheets comprising at least one active ingredient and at least one excipient through their thickness, wherein at least one excipient has a solubility in physiological fluid under physiological conditions no less than 30 g/l;
said sheets further comprising segments separated and spaced from adjoining segments by free spacings, said free spacings defining one or more interconnected free spaces between said sheets or segments thereof;

said one or more interconnected free spaces filled with at least a gas; and at least one of said one or more interconnected free spaces terminating at said outer surface, and extending over a length and width at least half the thickness of the drug-containing solid.

22. A pharmaceutical dosage form comprising:

an outer surface and an internal structure contiguous with and terminating at said outer surface;

said internal structure comprising a continuous, three dimensional structural framework of one or more sheets and one or more fibers or one or more beads;

said sheets comprising at least one active ingredient and at least one excipient through their thickness, wherein at least one excipient has a solubility in physiological fluid under physiological conditions no less than 1 g/l;

said fibers or beads bonded to and positioned between one or more sheets so that the sheets are separated and spaced from adjoining sheets by free spacings, said free spacings defining one or more interconnected free spaces between said sheets; and one or more interconnected free spaces filled with at least a gas and terminating at said outer surface.

\* \* \* \* \*